United States Patent
Watkins et al.

(10) Patent No.: US 9,976,973 B2
(45) Date of Patent: May 22, 2018

(54) COUNTING PARTICLES USING AN ELECTRICAL DIFFERENTIAL COUNTER

(75) Inventors: Nicholas Watkins, Attleboro, MA (US); Rashid Bashir, Champaign, IL (US); William Rodriguez, Cambridge, MA (US); Xuanhong Cheng, Bethlehem, PA (US); Mehmet Toner, Wellesley, MA (US); Grace Chen, Cambridge, MA (US); Aaron Oppenheimer, Cambridge, MA (US)

(73) Assignees: The General Hospital Corporation, Boston, MA (US); Massachusetts Institute of Technology, Cambridge, MA (US); The Board of Trustees of the University of Illinois, Urbana, IL (US); Daktari Diagnostics, Inc., Cambridge, MA (US)

( * ) Notice: Subject to any disclaimer, the term of this patent is extended or adjusted under 35 U.S.C. 154(b) by 545 days.

(21) Appl. No.: 13/884,580

(22) PCT Filed: Nov. 9, 2011

(86) PCT No.: PCT/US2011/060041
§ 371 (c)(1),
(2), (4) Date: Jul. 22, 2013

(87) PCT Pub. No.: WO2012/064878
PCT Pub. Date: May 18, 2012

(65) Prior Publication Data
US 2013/0295588 A1    Nov. 7, 2013

Related U.S. Application Data

(60) Provisional application No. 61/411,893, filed on Nov. 9, 2010.

(51) Int. Cl.
*G01N 15/10* (2006.01)
*G01N 27/02* (2006.01)
(Continued)

(52) U.S. Cl.
CPC ............ *G01N 27/02* (2013.01); *C12M 41/36* (2013.01); *G01N 15/12* (2013.01);
(Continued)

(58) Field of Classification Search
CPC ......... G01N 33/56972; G01N 15/1056; G01N 2015/129; G01N 2333/70514;
(Continued)

(56) References Cited

U.S. PATENT DOCUMENTS 2,656,508 A    10/1953    Coulter
5,155,044 A    10/1992    Ledis et al.
(Continued)

FOREIGN PATENT DOCUMENTS

CA    2518677    12/2004
CN    1050771 A    4/1991
(Continued)

OTHER PUBLICATIONS

Fu et al. "A microfabricated fluorescence-activated cell sorter", Nature Biotechnology, Nov. 17, 1999.*
(Continued)

*Primary Examiner* — Erik B Crawford
(74) *Attorney, Agent, or Firm* — Fish & Richardson P.C.

(57) ABSTRACT

This disclosure relates to methods and devices to count particles of interest, such as cells. The methods include obtaining a fluid sample that may contain particles of interest; counting all types of particles in a portion of the sample using a first electrical differential counter to generate a first total; removing any particles of interest from the portion of the fluid sample; counting any particles remaining in the portion of the fluid sample using a second electrical differential counter after the particles of interest are removed to generate a second total; and calculating a number of particles of interest originally in the fluid sample by sub-
(Continued)

tracting the second total from the first total, wherein the difference is the number of particles of interest in the sample. These methods and related devices can be used, for example, to produce a robust, inexpensive diagnostic kit for CD4+ T cell counting in whole blood samples.

2 Claims, 18 Drawing Sheets

(51) Int. Cl.
G01N 15/12 (2006.01)
C12M 1/34 (2006.01)
G01N 33/569 (2006.01)
G01N 15/14 (2006.01)
(52) U.S. Cl.
CPC ... *G01N 15/1245* (2013.01); *G01N 33/56972* (2013.01); *B01L 2200/0652* (2013.01); *B01L 2300/0877* (2013.01); *G01N 2015/1006* (2013.01); *G01N 2015/1486* (2013.01)
(58) Field of Classification Search
CPC ............. G01N 15/12; G01N 15/14; G01N 2015/1062; G01N 2015/1486; B01L 3/502761; B01L 2200/0668; B01L 2300/0645; B01L 3/5027; Y10T 436/101
See application file for complete search history.

(56) References Cited

U.S. PATENT DOCUMENTS

| | | | |
|---|---|---|---|
| 5,260,192 A | 11/1993 | Russell et al. | |
| 2003/0104486 A1 | 6/2003 | Selvan | |
| 2003/0190608 A1* | 10/2003 | Blackburn | B01J 19/0093 435/6.11 |
| 2003/0235917 A1 | 12/2003 | Li et al. | |
| 2007/0205747 A1* | 9/2007 | Cho | G01N 15/12 324/71.4 |
| 2009/0117555 A1* | 5/2009 | Kuypers | G01N 15/147 435/6.14 |
| 2009/0298067 A1 | 12/2009 | Irimia et al. | |
| 2010/0075340 A1 | 3/2010 | Javanmard et al. | |
| 2011/0028341 A1* | 2/2011 | Wang | G01N 15/147 506/9 |
| 2011/0275111 A1* | 11/2011 | Pettigrew | B01L 3/502776 435/29 |
| 2011/0312518 A1* | 12/2011 | Davis | B01L 3/502761 506/9 |
| 2012/0003687 A1* | 1/2012 | Toner | G01N 33/84 435/39 |
| 2012/0142032 A1* | 6/2012 | Morgan et al. | 435/7.24 |

FOREIGN PATENT DOCUMENTS

| | | |
|---|---|---|
| CN | 1829914 | 9/2006 |
| CN | 101379387 | 3/2009 |
| CN | 101443660 | 5/2009 |
| CN | 101535466 | 9/2009 |
| CN | 101583959 | 11/2009 |
| CN | 102239409 | 11/2011 |
| WO | WO1990/013013 | 11/1990 |
| WO | WO2003/006956 | 1/2003 |
| WO | WO2007/106598 | 9/2007 |
| WO | WO09/006456 | 1/2009 |
| WO | 2010/086786 | 8/2010 |

OTHER PUBLICATIONS

Rodrigues et al. "Cell-based microfluidic biochip for the electrochemical real-time monitoring of glucose and oxygen", Sensors and Actuators B, 132, 2008, 608-613.*

Cheng et al. "Cell detection counting through cell lysate impedance spectroscopy in microfluidic devices," Lab on a Chip, vol. 7, pp. 746-755, 2007.
Usami et al., "Design and construction of a linear shear stress flow chamber," Annals of Biomedical Engineering, vol. 21, No. 1, pp. 77-83, Jan. 1993.
Hinterdorfer et al., "Detection and localization of individual antibody-antigen recognition events by atomic force microscopy," Proceedings of the National Academy of Sciences of the United States of America, vol. 93, No. 8, pp. 3477-3481, 1996x.
Dammer et al., "Specific antigen/antibody interactions measured by force microscopy," Biophysical Journal, vol. 70, pp. 2437-2441, May 1996.
Harada et al., "Specific and quantized antigen-antibody interaction measured by atomic force microscopy," Langmuir, vol. 16, No. 2, pp. 708-715, Nov. 2000, abstract only, 1 page.
Sethu et al., "Continuous flow microfluidic device for rapid erythrocyte lysis," Analytical Chemistry, vol. 76, pp. 6247-6253, 2004.
Sethu et al., "Microfluidic isolation of leukocytes from whole blood for phenotype and gene expression analysis," Analytical Chemistry, vol. 78, pp. 5453-5461, 2006.
Holmes et al., "Leukocyte analysis and differentiation using high speed microfluidic single cell impedance cytometry," Lab on a Chip, vol. 9, pp. 2881-2889, 2009.
Cheung et al. "Microfluidic Impedance-Based Flow Cytometry," Cytometry: Part A, 2010, 77A, 648-666.
Sweryda-Krawiec et al., "A new interpretation of serum albumin surface passivation," Langmuir, vol. 20, pp. 2054-2056, Sep. 2004.
Freeman et al., "Real time, high resolution studies of protein adsorption and structure at the solid-liquid interface using dual polarization interferometry," Journal of Physics: Condensed Matter, vol. 16, pp. S2493-S2496, 2004.
Gawad et al., "Micromachined impedance spectroscopy flow cytometer for cell analysis and particle sizing," Lab on a Chip, 1(1) 76-82.
Office Action issued in Chinese Application No. 201180064558.0 dated Sep. 29, 2014, 26 pages (with English translation).
International Search Report and Written Opinion dated for corresponding application PCT/US2011/060041.
Watkins, N. N. et al., "A microfabricated electrical differential counter for the selective enumeration of CD4+ T lymphocytes". Lab Chip. Apr. 2011, vol. 11, No. 8, pp. 1437-1447.
Office Action issued in Chinese Application No. 201180064558.0 dated Jun. 1, 2015, 27 pages (with English translation).
European Search Report in International Application No. 11839117.6, dated May 3, 2016, 5 pages.
Lee et al., "A Flow Rate Independent Cell Contration Measurement Chip Using Electrical Cell Counters Across a Fixed Control Volume," Journal of Microelectromechanical Systems 17(1):139-146 (2008), 8 pages.
European Office Action in European Application No. 11839117.6, dated Apr. 5, 2017, 8 pages.
Office Action in Chinese Application No. 201180064558, dated Mar. 21, 2017, 19 pages (with English translation).
Sun and Morgan, "Single-cell microfluidic impedance cytometry: a review," Microfluid Nanofluid, 2010, 8: 423-443.
Office Action in Chinese Application No. 201180064558.0, dated Aug. 11, 2016, 23 pages (with English translation).
European Examination Report in International Application No. 11839117.6, dated May 31, 2016, 8 pages.
Ayliffe, "Electric Impedance Spectroscopy Using Microchannels with Integrated Metal Electrodes," J. Microelectromech. Systems, Mar. 1999, 8(1): 50-57.
Chen and Wang, "Optical microflow cytometer for particle counting, sizing and fluorescence detection," Microfluid. Nanofluid., 2009, 6: 529-537.
Cheng et al., "Enhancing the performance of a point-of-care CD4+ T-cell counting microchip through monocyte depletion for HIV/AIDS diagnostics," Lab Chip, May 2009, 9: 1357-1364.
Cheng et al, "A microchip approach for practical label-free CD4+ T-cell counting of HIV-infected subjects in resource-poor settings," J. Acq. Imm. Def. Synd., Jul. 2007, 45(3): 257-261.

(56) References Cited

OTHER PUBLICATIONS

Cheng et al., "A microfluidic device for practical label-free CD4+ T cell counting of HIV-infected subjects," Lab Chip, Feb. 2007, 7: 170-178.
Cheung et al., "Impedance Spectroscopy Flow Cytometry: On-Chip Label-Free Cell Differentiation," Cytom. Part A, 2005, 65A: 124.
Gawad et al., "Dielectric spectroscopy in a micromachined flow cytometer: theoretical and practical considerations," Lab Chip, 2004, 4: 241-251.
Lin et al., "Microfluidic cell counter/sorter utilizing multiple particle tracing technique and optically switching approach," Biomed Microdevices, 2008,10: 55-63.
Morgan et al., "High speed simultaneous single particle impedance and fluorescence analysis on a chip," Curr. Appl. Phys., 2006, 6(3): 367-370.
Morgan et al., "Single cell dielectric spectroscopy," J. Phys. D. Appl. Phys., 2007, 40: 61-70.
Satake, "A sensor for blood cell counter using Mems technology," Sensor and Actuators B-Chem., 2002, 83: 77-81.
Sohn et al., "Capacitance cytometry: Measuring biological cells one by one," PNAS, 2000, 97(20): 10687-10690.
Sun et al., "High speed multi-frequency impedance analysis of single particles in a microfluidic cytometer using maximum length sequences," Lab Chip, 2007, 7: 1034-1040.
Takahashi, "Non-destructive on-chip cell sorting system with real-time microscopic image processing," J. Nanobiotechnol., Jun. 2004, 2:5.
Wang et al., "On-chip counting the number and the percentage of CD4+ T lymphocytes," Lab Chip, 2008, 8: 309-315.
Wolff et al., "Integrating advanced functionality in a microfabricated high-throughput fluorescent-activated cell sorter," Lab Chip, 2003, 3: 22-27.
Wu et al., "Simultaneous particle counting and detecting on a chip," 2008, 8: 1943-1949.
Wu et al., "Microfluidic differential resistive pulse sensors," Electrophoresis 29(13): 2754-2759.
Holmes and Morgan, Single Cell Impedance Cytometry for Identification and Countiing of CD4 T-Cells in Human Blood Using Impedance Labels, Anal. Chem., Feb. 2010, 82: 1455-1461.
Indonesian Office Action in Application No. WO0201302003, dated Jul. 17, 2017, 2 pages (with English translation).
Canadian Office Action in Application No. 2,817,311, dated Nov. 27, 2017, 4 pages.
Chinese Office Action in Application No. 201180064558.0, dated Aug. 28, 2017, 19 pages (with English translation).

\* cited by examiner $V_{OUT} = V_1 - V_2$

COUNTING PARTICLES USING AN ELECTRICAL DIFFERENTIAL COUNTER

CROSS-REFERENCE TO RELATED APPLICATIONS

This application is a 371 U.S. National of International Application No. PCT/US2011/060041, filed Nov. 9, 2011, which claims the benefit of U.S. Provisional Application No. 61/411,893, filed on Nov. 9, 2010, which is incorporated herein by reference in its entirety.

This invention was made with Government support under Grant Number EB002503 awarded by the National Institutes of Health. The Government has certain rights to this invention.

TECHNICAL FIELD

This invention relates to counting particles such as cells, and more particularly to counting particles using electrical differential counters.

BACKGROUND

Counting of particles, such as cells, is of significant use in medicine and public health. One widely used cytometry system involves optical devices, such as flow cytometers, and tags cells of interest with optical labels (such as fluorescent markers) and interrogates them with light sources such as lasers.

The Coulter principle of impedance cytometry, based on resistive-pulse sensing, is well-established for counting cells non-optically. In its original format, Coulter counting allowed for differentiation of cells by size, to enable counting of individual subsets of a mixed population, such as a white blood cell differential. A second generation of impedance spectroscopy methods builds on the original Coulter principle and interrogates cells across a sweep of alternating current (AC) frequencies.

Microfluidic systems have shown unique promise for studying cell function, cell and tissue engineering, disease diagnosis, blood sample preparation, and drug discovery. Very recently, the use of microfluidics to isolate pure populations of leukocyte subsets from whole blood has attracted significant interest for point-of-care diagnostics. While the principle behind a cell isolation approach can be easily adapted to a wide spectrum of clinical applications, detecting these isolated cells remains a technical challenge to be addressed.

SUMMARY

This disclosure describes systems and methods for counting particles of interest in a mixed population of particles using a simple, low-cost electrical method. Using a differential counting method with an electrical differential counter, these systems and methods can be used to count a subset of particles, e.g., white blood cells, from a starting sample, e.g., of whole blood, beyond the capability of current Coulter type systems and methods. For example, systems with two electrical impedance sensors can be used to obtain an absolute CD4+ T cell count from a blood sample.

In one aspect, the disclosure includes methods of counting particles of interest, such as cells, e.g., white blood cells, e.g., CD4+ T cells, in a sample, e.g., whole blood, that includes two or more different types of particles. These methods include obtaining a fluid sample that may contain particles of interest; counting all types of particles in a portion of the sample using a first electrical differential counter to generate a first total; removing any particles of interest from the portion of the fluid sample; counting any particles remaining in the portion of the fluid sample using a second electrical differential counter after the particles of interest are removed to generate a second total; and calculating a number of particles of interest originally in the fluid sample by subtracting the second total from the first total, wherein the difference is the number of particles of interest in the sample.

In these methods, the first and second electrical differential counters can be the same or a different electrical differential counter. In some implementations, these methods can further include reversing a flow direction of the fluid sample after removing the particles of interest from the portion of the fluid sample. In other implementations, the methods can further include maintaining a flow direction of the fluid sample while counting all types of particles in the portion of the sample; removing particles of interest; and counting any particles remaining in the portion of the fluid sample. In these methods, the particles, e.g., cells, of interest are removed from the portion of the fluid sample using one or more binding agents or moieties, such as antibodies, e.g., that specifically binds to a specific surface marker on the particle of interest, such as a white blood cell, such as a CD4+ T cell, or a particulate type of white blood cell, or a platelet, or other specific cell in the sample, such as a tumor cell, e.g., a circulating tumor cell (CTC).

In other implementations, the methods can further include depleting selected particles from the portion of the sample before counting all types of particles in the portion of the sample. For example, if the sample is whole blood, the method can include depleting erythrocytes in the blood using a lysis technique. In other implementations, for example, the fluid sample can include whole blood and the method can include depleting erythrocytes, monocytes, neutrophils, CD8+ lymphocytes, or other cellular components of blood by immuno-depletion.

In certain implementations, the particles of interest are CD4+ T cells, and removing the particles of interest includes capturing CD4+ T cells in a capture chamber functionalized with anti-CD4 antibodies. The methods can further include removing non-specifically adsorbed leukocytes by purging the capture chamber with phosphate buffered saline. The methods can also further include determining a cell flow direction based on a polarity of an impulse signal generated by the first electrical differential counter.

In another aspect, the disclosure includes devices that include a microfluidic chip defining a channel including an inlet and an outlet; a capture chamber arranged along the channel between the inlet and the outlet, wherein the chamber is configured to capture particles of interest from fluid flowing through the channel; a first electrical differential counter arranged to count all types of particles in a fluid flowing into the capture chamber; a second electrical differential counter arranged to count all types of particles remaining in the fluid flowing out of the capture chamber; and a computing mechanism in electronic communication with the first and second electrical differential counters, wherein the computing mechanism calculates a number of particles of interest based on signals from the first and second electrical differential counters.

In different implementations of these devices, the first and second electrical differential counters can be the same or different electrical differential counters. The devices can further include a pump system in fluid communication with the channel, wherein the pump system is operable in a first mode to cause fluid to flow in a first direction in the channel past the first electrical differential counter and operable in a second mode to cause fluid to flow in a second direction in the channel opposite the first direction and back to the first electrical differential counter.

In certain implementations, a portion of the channel can define a flow path that extends in a loop from the first electrical differential counter through the capture chamber and back to the first electrical differential counter.

In various implementations, the capture chamber includes surfaces functionalized with binding agents, such as anti-CD4 antibodies.

In another aspect, the disclosure includes kits that include a device as described herein; a solution that includes a binding agent or moiety, such as an antibody, e.g., that specifically binds to a specific surface marker on a white blood cell, such as a CD4+ T cell, with an affinity for the particles of interest; and a solution comprising a lysing agent effective to lyse selected particles without lysing the particles of interest. In the devices in these kits, the first and second electrical differential counters can be the same or different electrical differential counters, and the devices can further include a pump system in fluid communication with the channel, wherein the pump system is operable in a first mode to cause fluid to flow in a first direction in the channel past the first electrical differential counter and operable in a second mode to cause fluid to flow in a second direction in the channel opposite the first direction back to the first electrical differential counter.

In some implementations, a portion of the channel defines a flow path that extends in a loop from the first electrical differential counter through the capture chamber and back to the first electrical differential counter.

In another aspect, the disclosure describes microfluidic chips that include a plurality of capture chambers, wherein the capture chambers are configured to capture particles of interest from fluid flowing through the chambers; an electrical differential counter operable to count particles in a mixed population of particles in fluid flowing into the capture chambers and to count particles remaining in fluid flowing out of the capture chamber; and a computing mechanism in electronic communication with the electrical differential counter, the computing mechanism operable to calculate a number of particles of interest based on signals from the electrical differential counter.

These microfluidic devices can further include a fluidic channel coupled to the plurality of chambers, wherein the fluidic channel includes a first channel region and a second channel region, wherein the first channel region is configured to receive a lysing solution and a sample fluid, and mix the sample fluid with the lysing solution, and wherein the second channel region is configured to receive a quenching solution and a lysed solution from the first channel region, and mix the quenching solution with the lysed solution.

In any of the forgoing aspects and implementations, the binding agents or moieties can be selected from antibodies, antibody fragments, oligo- or polypeptides, nucleic acids, cellular receptors, ligands, aptamers, MHC-peptide monomers or oligomers, biotin, avidin, oligonucleotides, coordination complexes, synthetic polymers, and carbohydrates.

Also in any of the forgoing aspects, the sample can be a blood sample, the binding moiety can bind to CD66, CDI4, CD4, CDS, EpCAM, E-Selectin, or P-Selectin, and the desired cell can be selected from neutrophils, monocytes, lymphocytes, circulating tumor cells (CTCs), HIV infected CD8 lymphocytes, circulating endothelial cells, and platelets. In some implementations, the desired cells of interest are CD4+ lymphocytes. In this implementation, the sample may be obtained from a patient at risk of developing AIDS.

By a "patient" is meant a living multicellular organism. The term "patient" is meant to include humans, mice, dogs, cats, cows, sheep, horses, non-human primates, and fish.

By "binding moieties" or "binding agents" is meant a molecule that specifically binds to an analyte (e.g., a cell). Binding moieties include, for example, antibodies, aptamers, receptors, ligands, antigens, biotin/avidin, metal ions, chelating agents, nucleic acids, MHC-peptide monomers, tetramers, pentamers, or other oligomers.

By "cell surface marker" is meant a molecule bound to a cell that is exposed to the extracellular environment. The cell surface marker can be a protein, lipid, carbohydrate, or some combination of the three. The term "cell surface marker" includes naturally occurring molecules, molecules that are aberrantly present as the result of some disease condition, or a molecule that is attached to the surface of the cell.

By "lysis" is meant disruption of the cellular membrane. For the purposes of this invention, the term "lysis" is meant to include complete disruption of the cellular membrane ("complete lysis"), partial disruption of the cellular membrane ("partial lysis"), and permeabilization of the cellular membrane.

By "binding moiety" is meant a chemical species to which a cell binds. A binding moiety may be a compound coupled to a surface or the material making up the surface. Exemplary binding moieties include antibodies, antibody fragments (e.g., Fe fragments), oligo- or polypeptides, nucleic acids, cellular receptors, ligands, aptamers, MHC-peptide monomers or oligomers, biotin, avidin, oligonucleotides, coordination complexes, synthetic polymers, and carbohydrates.

The term "chamber" is meant to include any designated portion of a micro fluidic channel, e.g., where the cross-sectional area is greater, less than, or the same as channels entering and exiting the chamber.

The methods and devices described herein provide several benefits and advantages. In particular, the approaches described herein can be used to provide novel devices for cell analysis that are smaller, less expensive, and simpler to use than presently existing large, expensive, and complex flow cytometers, Coulter counters and impedance spectroscopes. The devices described herein can be used to discriminate a wider number of cell types and subtypes than currently known Coulter counters and impedance spectroscopes. The smaller, less expensive, microfabricated devices described herein can require much smaller volumes of blood or plasma and expensive reagents. They can be less expensive to operate and maintain. These devices represent mobile platforms that can be used at the point of care, independent of health care infrastructure. As closed, one-time use, disposable devices for the handling of blood and other biohazardous fluids, these devices reduce system risks and costs. Thus, the new methods and devices can be used to diagnose various diseases such as HIV/AIDS and cancers such as leukemia, and can be used to monitor a patient's progress with medication, e.g., to determine the overall efficacy of a particular treatment regimen used for a given patient.

Compared to optical cytometry methods, the simplicity of the electrical interrogation methods as described herein, and extended to multi-frequency impedance methods can be used to create a more streamlined, cost-effective, and mechanically robust solution for portable cellular analysis. The devices described herein are simpler and less expensive, in part, because they do not require a stable light path and the associated lensing, filtering, and focusing mechanisms that can add cost and complexity to optical detection methods. Moreover, the devices described herein can have higher throughput, than optical detection devices, which tend to have low throughput because of the small detection area available at a single time.

The microfabricated cell counters described herein are unlike Coulter counters, in that they can be used to count complex subsets of cells in a simple, handheld system without the need for external cell surface labels and other reagents, which add complexity and cost to the assay. Moreover, unlike cell counting strategies like flow cytometry and impedance measurement, the microfabricated cell counters described herein can be used with cells attached to surfaces even to count small numbers of cells on large surface areas in a relatively large volume.

Detection and enumeration of cells are essential for medical diagnostics, especially for AIDS and cancer diagnosis, and pathogen detection. While most existing methods to detect cells are optical (i.e., microscopy), electrical detection is significantly simpler, cheaper, and more amenable to point-of-care devices. To date, electrical detection and enumeration of intact cells based on impedance spectroscopy (i.e., detection of changes in electrical impedance caused by the presence of cells) have proven to be extremely practical and inexpensive, but limited to large cell populations or homogenous cell types (e.g., Coulter counting of red blood cells or total lymphocytes).

The combination of selective particle depletion in a microfluidic device using controlled shear flow, with double counting provides the new particle counting systems based on a subtraction assay concept. Both the microfluidic particle capture methods and the resistive pulse particle count methods are extremely robust and simple, and can thus be used to produce a robust, inexpensive diagnostic kit, e.g., for CD4 cell counting. For example, referring to FIG. 1, a droplet of whole blood provided by a finger stick can be applied to the inlet of a chip incorporating the cell counting techniques described herein. Red blood cell lysis and absolute CD4+ T cell counting, as well as on-chip sample preparation for a subsequent viral load test, can be performed on the chip.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 20A shows results from 14 CD4+ T cell counting experiments using white blood cells purified from human whole blood samples and the close correlation (y=0.994x, R2=0.997) between the electrical differential method and the optical control.

FIG. 21 illustrates how the percent error (absolute difference in optical and electrical counts, normalized by the CD4+ T cell count) relates to the total number of CD4+ T cells counted.

FIG. 23A shows differential counts vs. trigger level and shows stability between 8× and 12× trigger levels. Slope FIG. 23B and curvature FIG. 23C analysis identifies 12× as the optimal trigger level because it is part of the most stable regime in the curve.

Like reference symbols in the various drawings indicate like elements.

DETAILED DESCRIPTION

The new systems and methods are based on a simple and low-cost electrical counting method and can be used to count particles of interest in a mixed population of particles in a sample, such as a fluid sample, or a particulate sample dispersed in a fluid. Using differential counting methods with an electrical differential counter, these systems and methods can be used to count a subset of white blood cells from a starting sample of whole blood. For example, systems with two electrical impedance sensors can be used to obtain an absolute CD4+ T cell count from a blood sample.

The new micro-scale devices operate using a novel subtraction impedance interrogation technique. In the described methods, a complex mixture of particles in a starting sample is passed through an electrode configuration for resistive-pulse or impedance sensing, and a total count of particles in the collective starting sample can be obtained. Next, particles of interest can be selectively retained in a microchannel through the use of a specific, immobilized capture reagent under controlled shear flow. Finally, the remaining population of particles in suspension can be passed through a second electrode configuration for resistive-pulse sensing, and a second count of the total population, depleted of the particles of interest, can be obtained. The difference between the two counts represents the count of the captured particles, and thus, the particle count of interest.

This approach can be used, for example, in a CD4+ T cell micro-cytometer, which is a micro-scale device for CD4+ T cell counting and which can be used as part of a kit for use in a point-of-care system for monitoring CD4+ T cell counts. In this implementation, whole blood is passed through an electrode sensing region, and the total particle count is obtained for the collective starting sample. The CD4+ T cells in the sample are selectively depleted through the use of anti-CD4 antibodies, immobilized in a microfluidic chamber or channel under controlled shear flow. The remaining population of particles in the CD4+ T cell depleted whole blood is passed then through a second electrode sensing region, and a second count of the total population depleted of the particles of interest is obtained. The difference between the two counts represents the count of the captured CD4+ T cells. This kit, device, and method can be used for counting CD4+ T cells from a finger stick of blood at the point of care.

Figure 1:
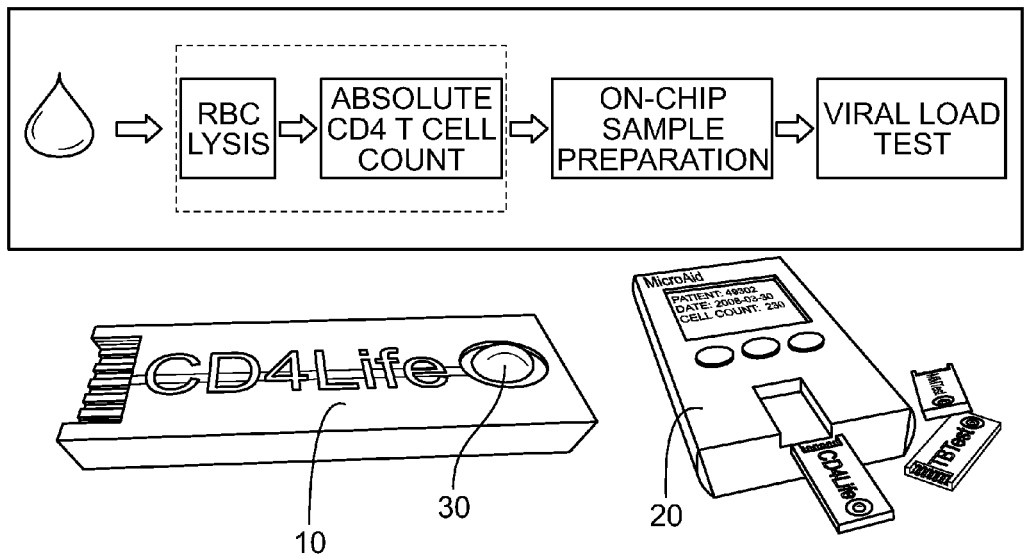
FIG. 1 is a schematic of a cell counting method and device, including test cartridges that include the microfluidic chips described herein.

As shown in FIG. 1, the device can be fully realized as (1) a one-time use, disposable cartridge 10 that contains all the microfluidics and sensing elements described herein, and (2) a hand-held cartridge reader 20, which provides the electrical sensing, stimuli, and fluidic controls (e.g., pumping mechanisms). The top of FIG. 1 also shows a flow diagram of the path of a droplet of whole blood, e.g., provided by a finger stick, from application to the inlet of a device (e.g., a sample cartridge and reading unit) incorporating the cell counting techniques described herein. The blood passes through a red blood cell lysis station and an absolute CD4+ T cell counting station, as well as an on-chip sample preparation station and a subsequent viral load test station.

As shown in FIG. 1, the drop of blood 30 (~10 to 20 µL volume) would be dropped onto the cartridge's receiving port after (or before) the cartridge 10 is inserted into the reading unit 20. The reading unit 20 would control the infusion of the blood and other fluids through the cartridge in addition to applying the electrical signal to the cartridge's sensing region and reading the change in the electrical signal caused by the passage of cells through the cartridge 10. The reading unit 20 would then analyze the electrical signals and calculate the concentration of the target cells, which would be displayed to the operator. As discussed in more detail below, different cartridges can be designed to sense for different diseases simply by changing the binding agent, e.g., antibody type, in the chip's capture region.

A Cell Counting Device in Operation

Use of an exemplary cell counting device 100 is illustrated in FIGS. 2A-2E. Cell counting device 100 includes two impedance sensors 110 and 111. The cell counting device 100 defines a microfluidic circuit or channel 112, which extends from a sample inlet 114 through a selective particle depletion chamber or capture chamber 116 to a sample outlet 118. The sample inlet 114 receives an unprocessed or a processed sample to be analyzed. The following discussion describes the use of cell counting device 100 to count CD4+ T cells in a sample of whole blood. Cell counting devices as described herein can also be used to analyze other samples including, for example, plasma, urine, sputum, or other biological or other fluids, e.g., industrial fluids, that contain two or more different types of particles.

Cell counting device 100 includes an optional reagent inlet 120, where one or more sample processing reagents can be introduced and mixed with the sample. In some instances, reagents introduced through this manner can be red blood cell lysing reagents, sample stabilization reagents, particle surface labels, or other reagents of interest.

Channel 112 can include an optional sample processing area 122, where the starting sample can be further processed or purified to make particle counting faster, more accurate, or more efficient. In cell counting device 100, the sample processing area 122 is a red blood cell lysis area and a monocyte depletion area. For example, the sample processing area 122 can include surfaces coated with a monocyte capture reagent such as an anti-CD14 antibody. In general, the capture chambers are functionalized or coated with binding agents or binding moieties as described herein. These binding moieties are selected to specifically bind to the particles, e.g., to surface markers on cells, and not to other particles that may be present in the sample. The sample processing area 122 can be a red blood cell lysis area, or a monocyte depletion area, or both.

Impedance sensors 110 and 111 are located in channel 112 on each side of capture chamber 116. Impedance sensors 110 and 111 are electrode configurations for the counting of particles in fluid flowing through the channel 112. The impedance sensors 110 and 111 can be two-electrode or three-electrode resistive pulse sensors of the Coulter type, for the counting of blood cells. The current implementation uses a coplanar electrode configuration, meaning all electrodes are on the same surface, and an AC signal is being passed between the electrodes. In other implementations, the impedance sensors 110 and 111 may be configured where each electrode and its mate are parallel to each other (still perpendicular to fluid flow direction), but one electrode is on the floor of the chamber while the other is on the ceiling of the chamber. The electrodes could also be placed parallel to each other, but at the sides of the channel (still perpendicular to the flow of cells). Another implementation is a fluidic electrode, where an electrical signal is passed through a small channel with a conductive solution that flows perpendicularly to the cell flow direction. The electrical leads in this case could be microfabricated or metal wires placed in each end of the fluidic electrode channel.

In addition, an AC (alternating current) or DC (direct current) signal can be used to sense cell passage. For a DC signal, Ag—AgCl (silver/silver chloride) electrodes could be used, as they provide excellent redox reaction efficiency even under high electrical current. In other implementations, the impedance sensors 110 and 111 can be, for example, capacitive sensors, resistive sensors, or other sensor modalities that measure the intrinsic optical or magnetic properties of the cells in a label free manner, or sensor modalities that measure labels associated with the cells.

Capture chamber 116 is a selective particle depletion or capture chamber, where particles of interest are selectively captured onto a surface or surfaces of the chamber using binding moieties such as analyte capture or binding agents and controlled shear, substantially as described in US 2009/0298067 A1, "Devices and Methods for Detecting Cells and Other Analytes" (which is incorporated herein in its entirety). In some implementations, capture chamber 116 is functionalized with anti-CD4 antibodies and serves as a selective CD4+ T cell depletion chamber. Of course, capture chamber 116 can be functionalized with any other binding agents, e.g., antibodies, aptamers, and binding pairs, which selectively bind to the specific particle or particles of interest. Such binding agents are known, or can be easily determined, for a given particle, e.g., cell, of interest.

In some implementations, the cell counting device 100 includes an optional fluidic entry channel 124 for sending reagents into the capture chamber 116 and an optional fluidic exit channel 126 for removing reagents sent into the capture chamber 116. The optional fluidic entry channel 124 and the optional fluidic exit channel 126 can be used, for example, to selectively functionalize the chamber with binding moieties.

The sample outlet 118 collects flow-through sample and sends it downstream, for example to a self-contained waste area. In some instances, the sample outlet 118 collects flow-through sample and sends it downstream to a downstream assay, or a further processing area on the microfluidic chip.

In some implementations, the cell counting device 100 also includes an optional selective sample processing area 128, where the sample is processed prior to mixing with reagents introduced through the reagent entry inlet 120. For example, the selective sample processing area 128 can be a selective filtration area where unwanted particles are filtered mechanically or chemically.

Before use, the cell counting device 100 is prepared by using the fluidic entry channel 124 and the fluidic exit channel 126 to selectively functionalize the capture chamber 116 with a binding agent, e.g., an antibody specific to the CD4 antigen that resides on the surface of the helper T cells and monocytes (though containing an order of magnitude less than the helper T cells.

Figure 2A:
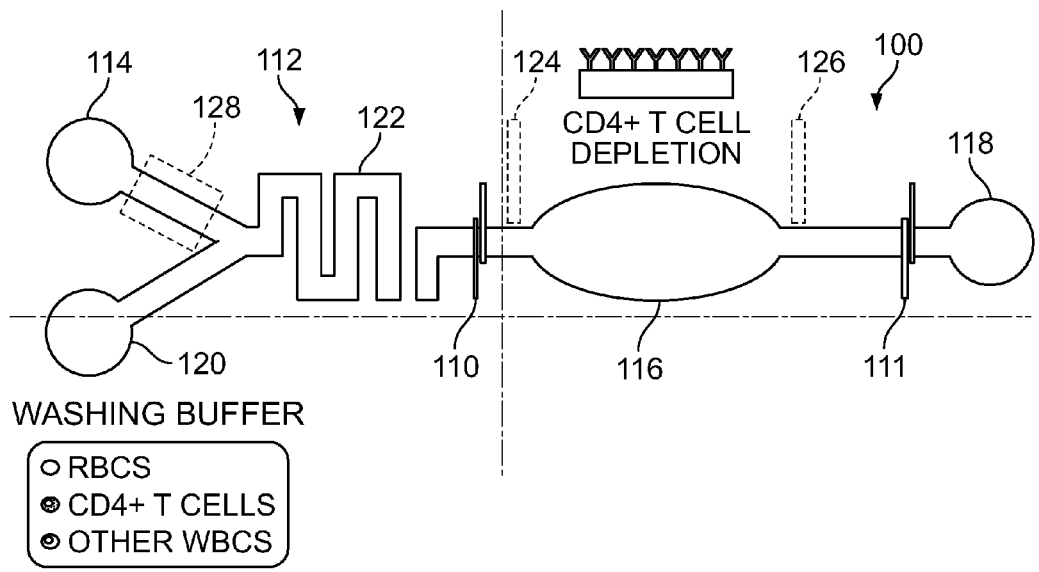
FIGS. 2A-2E are schematics of use a microfluidic circuit in a cell counting device.
Figure 2B:
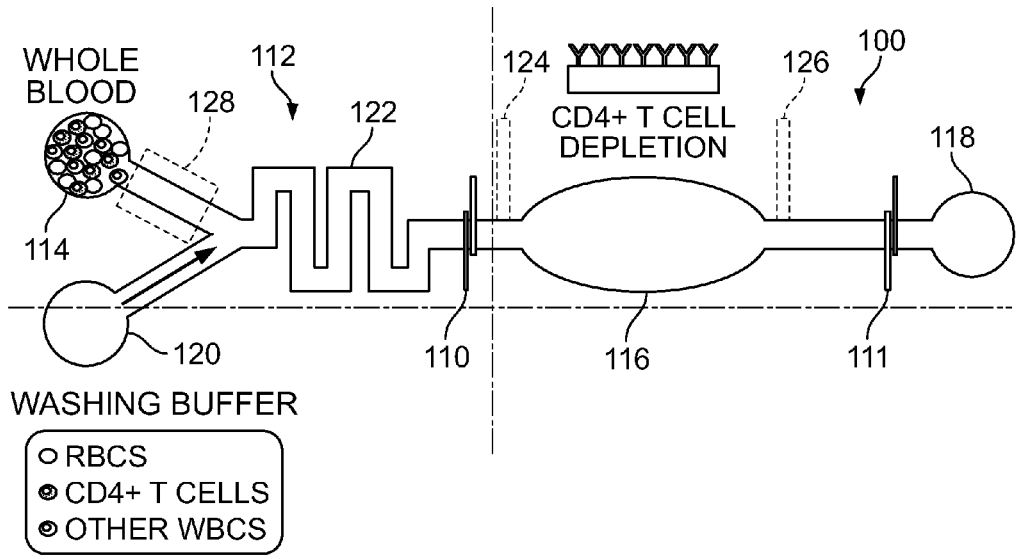
Figure 2C:
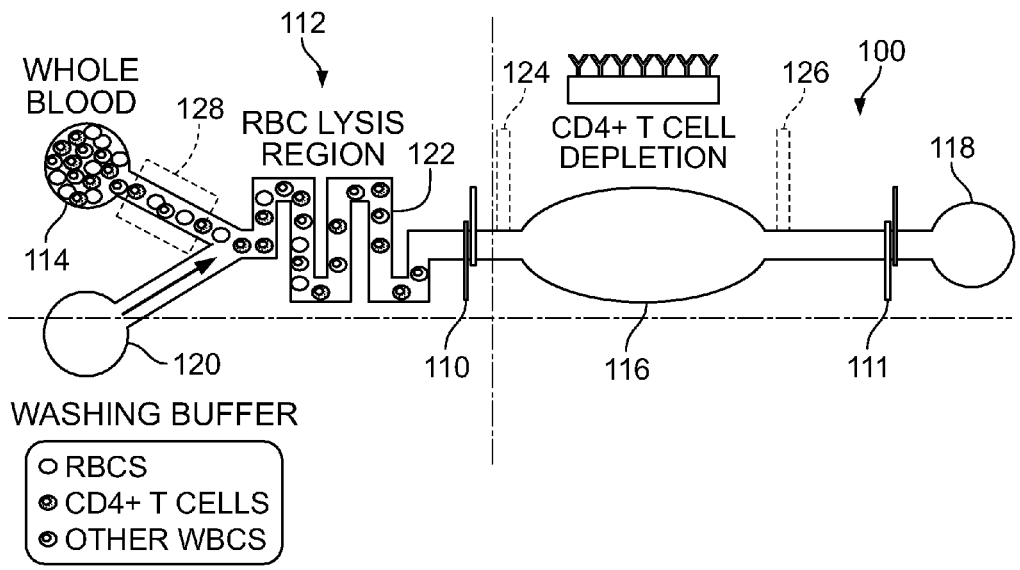
Figure 2D:
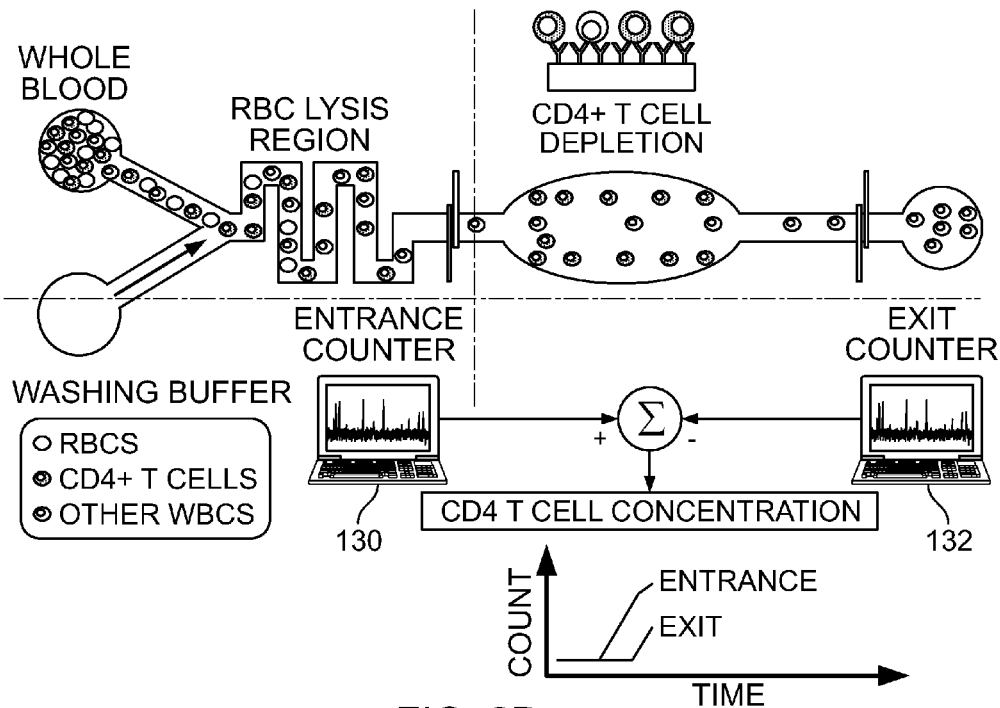
Figure 2E:
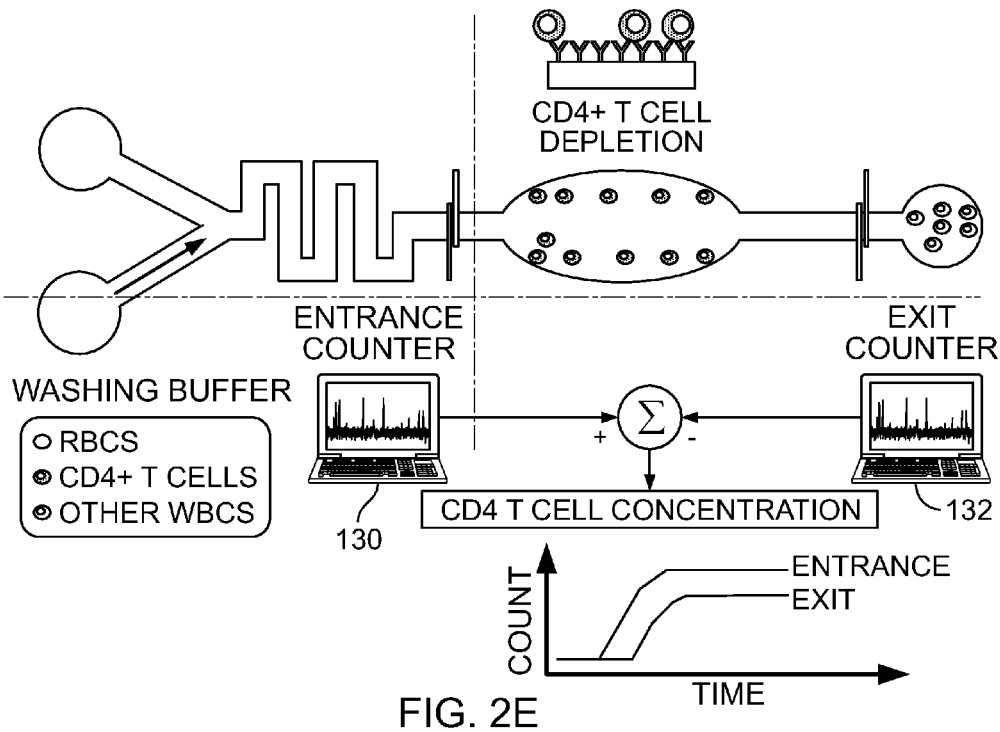

In use, the sample, e.g., whole blood is introduced into the cell counting device 100 through the sample inlet 114 and a chemical to lyse the red blood cells is introduced into the cell counting device 100 through the reagent inlet 120 (see FIG. 2B). Flowing through the sample processing area 122, red blood cells are lysed as the whole blood mixes with the red blood cell lysing agent and monocytes are captured on surfaces coated with a monocyte capture reagent such as an anti-CD14 antibody (see FIG. 2C). All white blood cells are counted as they pass the entrance impedance sensor 110. The enumerated cells enter a large capture chamber 116 that is functionalized with an antibody specific to the CD4 antigen. The capture chamber 116 retains CD4 T cells and monocytes while the remainder of the white blood cells exit the capture chamber 116 and are enumerated by the exit counter 111 (see FIG. 2D). PBS can then be introduced through reagent inlet 120 to wash away non-specifically bound cells in the capture chamber 116. A first electronic processor 130 is linked to the first electrode configuration 110, and records individual particle signals as resistive pulses or other electrical measurements. A second electronic processor 132 is linked to the second electrode configuration 111, and records individual particle signals as resistive pulses or other electrical measurements. With a known sample volume, the concentration of helper T cells can be obtained by finding the difference between the entrance and exit counts (see FIG. 2E).

This method can be adapted to count other cell types simply by choosing different antibodies for the particular cell surface antigen. The red blood cell lysis region can increase throughput, as erythrocytes' have a concentration of $5 \times 10^9$/mL in whole blood, which would prove quite difficult to count in a timely manner necessary for a global health diagnostics application. In addition, the sensitivity and accuracy in finding helper T cell counts would be severely diminished by the presence of the red blood cells. For example, if 10 μL of blood sample is analyzed, approximately $5 \times 10^7$ red blood cells, $1 \times 10^5$ white blood cells, and $1 \times 10^4$ helper T cells (in a healthy adult) would be counted. Only 0.02 percent of the counted cells would be helper T cells, which could easily be masked by the non-ideal situation of red blood cells being counted at the entrance, but not at the exit (one reason being that some red blood cells non-specifically adsorb to the capture chamber). Removal of the red blood cells would increase the percentage of helper T cells to 10% out of the total cells counted, greatly increasing the chip's accuracy and precision in providing cell counts.

Design and Fabrication

Figure 3:
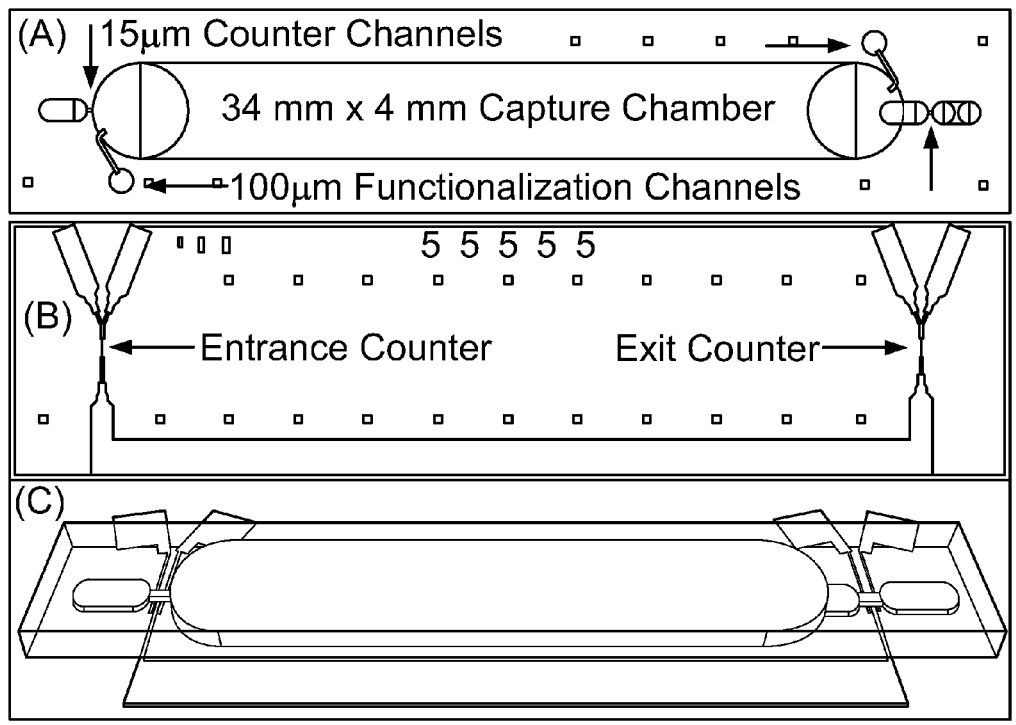
FIG. 3 is a schematic of a chip incorporating a cell counting device.

FIG. 3 shows a differential counter device 100 without the red blood cell lysis region 122. The fluidics layer (a) contains inlet and outlet ports for cell sample flow and two ports used to functionalize the 50 μm-high (6.6 μL) capture region with antibodies. The two impedance sensing regions are made with 15 μm-wide and 15 μm-high channels that funnel the cells over three 10 μm-wide platinum electrodes, spaced 10 μm apart (b). The height of the capture region was chosen to increase the volume of sample and ensure the proper shear stresses at the wall-fluid interface. According to Cheng et al. ("Cell detection counting through cell lysate impedance spectroscopy in microfluidic devices," Lab on a Chip, vol. 7, pp. 746-755, 2007), a shear stress of >3 dyn·cm$^{-2}$ resulted in less effective CD4 T cell capture. The equation $$\tau_\omega = \frac{6\mu Q}{h^2 \omega_1}$$

can be used to estimate the shear stress at the walls of a rectangular microfluidic channel of a constant width, $\omega_1$, where μ is the dynamic viscosity of the fluid, Q is the volumetric flow rate, and h is the height of the channel (Usami et al., "Design and construction of a linear shear stress flow chamber," Annals of Biomedical Engineering, vol. 21, no. 1, pp. 77-83, January 1993). This shows the sensitive, inverse-squared relationship between the channel height and the shear stress at the chamber's ceiling and floor. A 15 μm capture channel would give a shear stress of 10 dyn·cm$^{-2}$, well above the aforementioned maximum shear stress limit. This shear stress would create a force of −155 pN on a 10 μm cell's membrane, which is the same order of magnitude as the dissociation force of antibody-antigen interactions (see, e.g., Hinterdorfer et al., "Detection and localization of individual antibody-antigen recognition events by atomic force microscopy," Proceedings of the National Academy of Sciences of the United States of America, vol. 93, no. 8, pp. 3477-3481, 1996; Dammer et al., "Specific antigen/antibody interactions measured by force microscopy," Biophysical Journal, vol. 70, pp. 2437-2441, May 1996; and Harada et al., "Specific and quantized antigen-antibody interaction measured by atomic force microscopy," Langmuir, vol. 16, no. 2, pp. 708-715, November 2000).

A 50 μm capture channel height greatly reduces the average shear stress to 0.45 dyn·cm$^{-2}$, resulting in a force of −14 pN on the cell and greatly increasing the cell's surface antigen interactions with the immobilized Ab to facilitate cell capture. The 34 mm capture channel length ensures sufficient interaction time (about 80 seconds at sample flow rate of 5 jL·min$^{-1}$).

Three-dimensional hydrodynamic focusing was desired, but would have effectively increased the entrance flow rate 0125 μL/minute for a 5 μL/minute cell sample flow rate) and corresponding shear stress of 11.1 dyn·cm$^{-2}$, which is well beyond the maximum to facilitate CD4+ T cell capture. In addition, the cell passage time through the 15 μm×15 μm counter pore at this flow rate would result in transition times faster than 90 ns, which is well below the minimum transition time of ~2 μs that can be resolved using the lock-in amplifier described in the experimental section.

The fluidics and electrical sensing layers are then aligned and bonded to form the completed differential counter (c).

Figure 4:
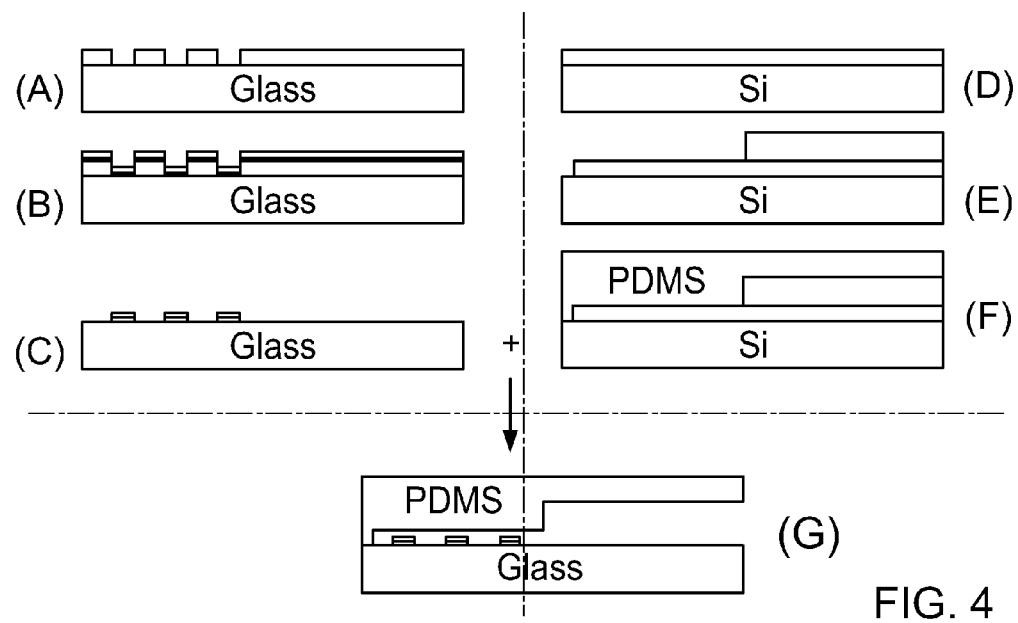
FIG. 4 is a schematic illustrating fabrication of a cell counting device.

Fabrication of the differential counter is illustrated for one counter region in FIG. 4. The electrical sensing layer can be fabricated using the standard metal lift-off process. A 4" glass wafer (Pyrex® 7740) is first spin-coated with LOR2A liftoff resist, soft-baked at 183° C. for 5 minutes and is coated with S-1805. After another soft-bake at 110° C. for 90 seconds, the wafer is aligned to the electrodes mask on a Quintel Q7000 IR backside mask aligner and exposed for a total dose of 2.8 mJ·cm$^{-2}$. The wafer is then placed on a 110° C. hotplate for a 60 seconds post-exposure bake before being immersed into Microposit MF CD-26 developer for 80 seconds and rinsed with DI water for 2 minutes (FIG. 4(a)). The wafer is then de-scummed in an $O_2$ plasma system for 20 seconds before being placed in a CHA Evaporator for the deposition of 25 nm of Ti seed layer, followed by a 75 nm Pt conduction layer (FIG. 4(b)). The undesired metal is lifted off by placing the wafer in a 70° C. bath of Microchem Remover PG for 15 minutes, creating the necessary conduction paths for the referenced counters (FIG. 4(c)).

The multi-height fluidics layer is created by fabricating a negative image of the desired channels using Microchem SU-8 25 photoresist. SU-8 25 is spun on a 4" Si wafer to a height of 15 μm, and is pre-baked in two steps for 2 minutes at 65° C. and then 95° C. for 5 minutes. The wafer is aligned and exposed to a mask defining all of the fluidic channels, including the capture region, counters, sample inlet and outlet, and Ab functionalization ports (FIG. 4(d)). A second layer of SU-8 is spun on to obtain a total thickness of 50 pm for the entire wafer, and is pre-baked at 65° C. for 5 minutes and then 95° C. for 15 minutes. The wafer is then exposed to a second mask only defining the capture chamber, allowing it to have a height of 50 pm, compared to the other fluidic regions of 15 pm in height. The wafer is developed in Microchem SU-8 developer for 2 minutes at room temperature, rinsed with isopropyl alcohol, and hard-baked at 125 65° C. for 15 minutes (FIG. 4(e)). Polydimethylsiloxane (PDMS), 1:10::curing agent:base, is poured over the negative mold and allowed to cure overnight at 65° C. (FIG. 4(f)). The polymerized mold is peeled off, and ports are punched for all inlets and outlets using a blunt syringe needle.

The sealed fluidic chip is completed by aligning and bonding the electrode sensing layer to the fluidics layer after oxygen plasma activation in a barrel etcher (FIG. 4(g)). Teflon microbore tubing is used to make fluidic connections between the chip and syringe pumps. The lysis region can be completed using the techniques described in Sethu et al. have shown that it is feasible to create a microfluidic red blood cell lysis device using diffusive mixing (see, e.g., Sethu et al., "Continuous flow microfluidic device for rapid erythrocyte lysis," Analytical Chemistry, vol. 76, pp. 6247-6253, 2004 and Sethu et al., "Microfluidic isolation of leukocytes from whole blood for phenotype and gene expression analysis," Analytical Chemistry, vol. 78, pp. 5453-5461, 2006).

Differential Counter Setup

Figure 5:
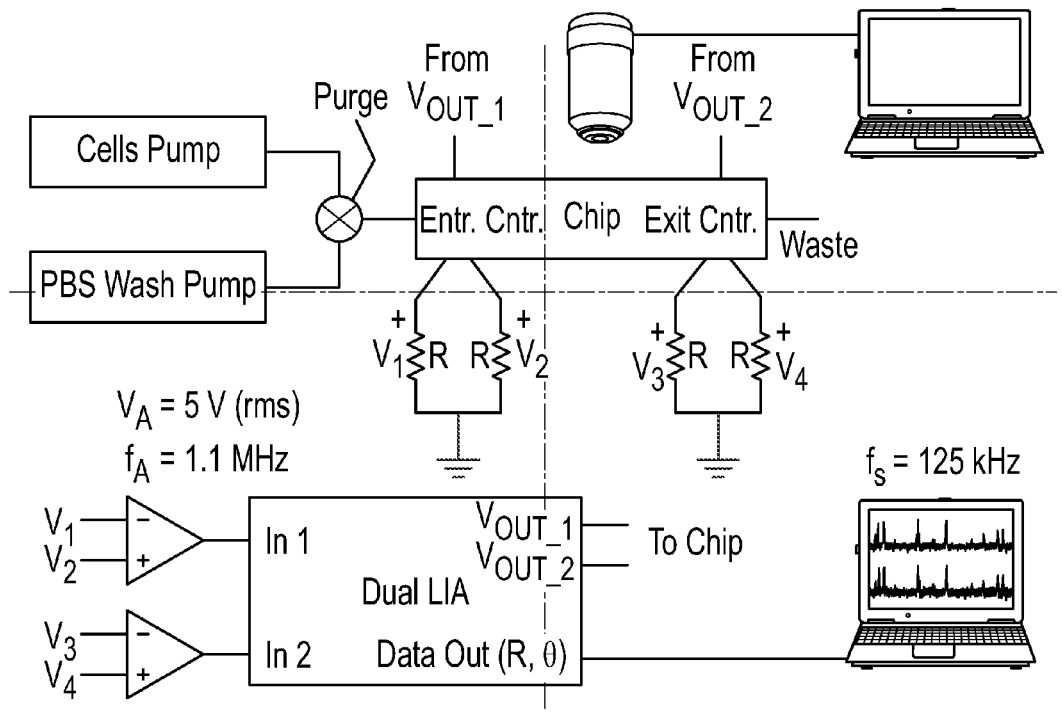
FIG. 5 is a schematic of a differential cell counter experimental setup.

FIG. 5 illustrates an example of a setup that can be used to differentially count CD4+ T cells. Initially, a pump, such as a Harvard Apparatus PicoPlus syringe pump, is used to flow a known volume of sample, e.g., white blood cells (from whole blood samples with lysed red blood cells), into the chip inlet and through the entrance counter, capture chamber, e.g., a CD4 Ab-functionalized capture chamber, and exit counter at a steady flow rate, e.g. 2, 3, 4, 5, 6, 7, 8, 9, or 10 μL/minute. After sample flow, PBS is pumped into the chip at a higher flow rate to remove any non-specifically bound cells from the capture chamber. An amplifier, e.g., a Zurich Instruments HF2LI dual lock-in amplifier, is used to inject an AC signal, e.g., a 5 V (rms) 1.1 MHz AC signal, into the exit and entrance sensors. Relative impedance is measured using a two-electrode arrangement that is self-referencing in a Wheatstone bridge configuration balanced with resistors and capacitors, e.g., 10 kΩ resistors (R) and a 68 pF capacitor.

Figure 6:
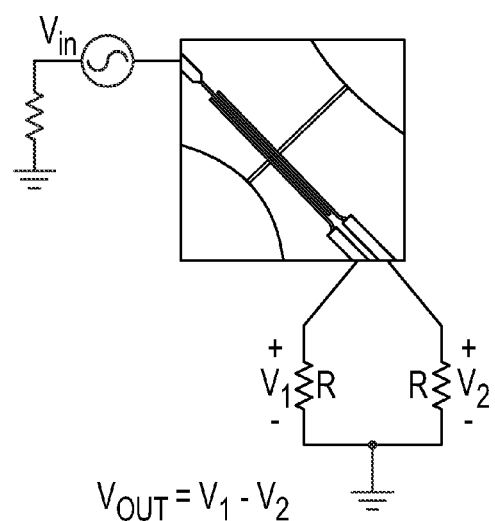
FIG. 6 is a circuit schematic of a self-referencing electrical sensor using three electrodes connected in a Wheatstone bridge configuration.

FIG. 6 provides a closer look at the balancing bridge configuration. When no particle is passing through the sensing region, the current on both branches is approximately the same, because both electrode impedances are similar and R is equal for both branches. Therefore, V1≈V2 and $V_{out}$ is ~0 V. When a cell passes through the sensor region (going from left to right), it will temporarily increase the impedance between the first and middle electrodes, reducing the current in the left branch and decreasing the voltage drop across V1, creating a negative pulse for V. The cell then passes between the middle and third electrode and conversely causes a positive pulse at V. As a result, each cell passage creates a down-up (or up-down, depending on the definition of $V_{out}$) pulse pair. This bridge balancing provides several benefits, including providing a baseline signal that varies little with changes to fluid conductivity or flow rate and providing a more sensitive detection method creating a larger impedance pulse signal-to-noise ratio. In addition, one can accurately determine whether cells are flowing past the sensor in a forward or reverse direction to ascertain total forward and reverse counts, respectively. Pulse polarity will reverse when direction reverses. Each cell passage creates either an up-down (or down-up) pulse signature in the forward flow direction, while in the reverse flow direction, all cells create down-up (or up-down) pulse signatures, respectively, enabling a straightforward method to differentiate between cells entering and exiting the chip.

The bridge potential difference signals for the entrance ($Vout_{out.1}$) and exit ($V_{out.2}$) are input into the amplifier, and the impedance magnitude and phase angle (R and θ, respectively) are output to a computer for real-time observation and recording of data, e.g., at a 115.2 kHz sampling rate using, for example, Lab-VIEW® software. The data is imported into and analyzed with Clampfit software. Impedance pulses can be counted using various threshold levels, and entrance and exit counts are compared. Another computer connected to a digital camera on a microscope, such as a Nikon Eclipse E600FN microscope (Nikon Instruments, Inc., Melville, N.Y.), can be used to observe cell passage through the channels as well as cellular interactions with the capture region.

Reverse-Flow Differential Counter

Although the shearing unit helps improve the operation of the differential counter device, another major problem arises in that it has proven difficult to objectively choose the correct trigger level for each counter to provide accurate counts. Ideally, both sensors should have the same electrical characteristics and require the use of the same trigger threshold levels. However, it seems that different threshold levels should be used, but several systematic methods to objectively choose the levels have failed (e.g., using triggers based on each electrode's baseline noise and calculating one counter's trigger level based on the weighted average of the other counter's pulse amplitude distribution). This may arise from the possibility that the electrical characteristics of each sensing region are different enough to cause an error in cell enumeration. Although microfabrication may provide entrance and exit counters with almost identical electrode geometries, other factors may cause each sensor to have different electrochemical properties. The metal lift-off procedure may leave nanoscale imperfections that vary from sensor to sensor, creating different field edge effects that may affect a counter's response to cell passage. Non-homogenous metal layer thicknesses from uneven evaporation (sometimes observed by a gradient in color of the metal layer through the entire die) would change the conductivity of the metal leads and the sensing region itself, especially between two counters on a single die that are separated by 34 mm. The connecting micromanipulator probing tips and external circuitry may also have different electrical characteristics between each branch. Some symptoms from these possible sources are (1) a counter's signal-to-noise ratio does not necessarily scale with its baseline's standard deviation, (2) differences between V0,t_1 and Vo,,t_2 for two sensors on the same chip, which should be the same, and (3) sometimes slowly changing Vo,,t_1 or Va,,,t2 values over time may point to electrochemical reactions occurring at the electrode-electrolyte interface.

Figure 11:
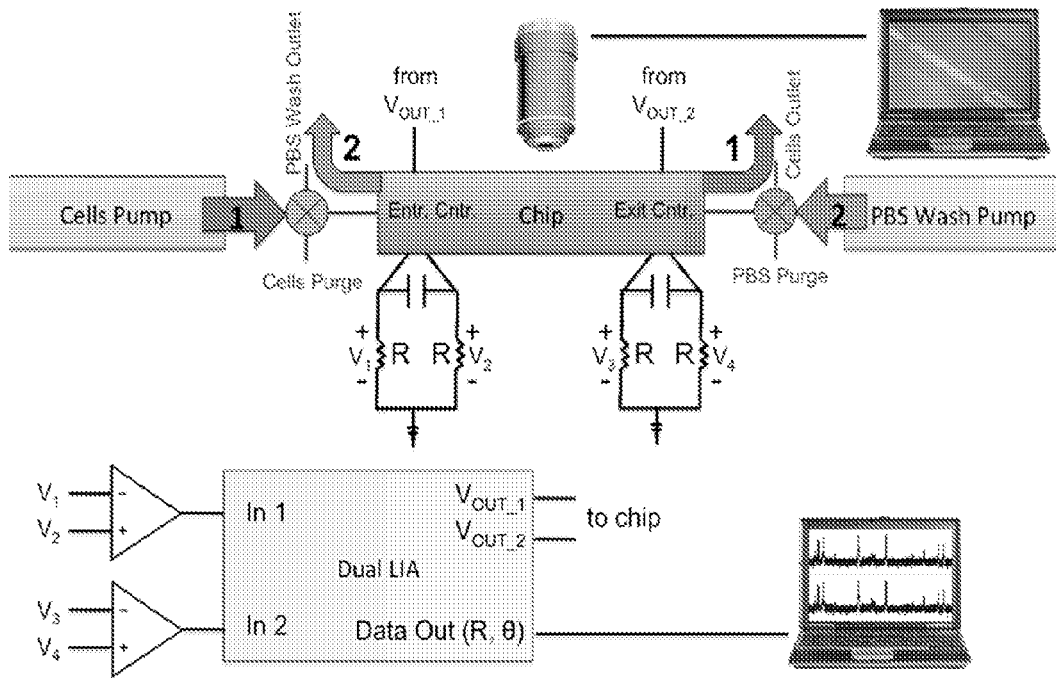
FIG. 11 is a schematic of a differential cell counter experimental setup based on a reverse flow concept using of a single pair of electrodes for a differential CD4+ T cell count.

To solve this threshold ambiguity problem, a single sensor can be used. FIG. 11 illustrates the concept of flowing white blood cells through the entrance of the chip and reversing the flow to push the cells back out the entrance. Cells are injected into the entrance port and flow into the functionalized capture chamber to capture helper T cells. When pulses are observed at the exit counter, the fluidic valves are switched to allow PBS to flow through the chip via the exit port, forcing all unattached cells to be counted again through the entrance counter. Washing continues until all unattached cells are washed from the chip. Because this method only uses the entrance counter to enumerate white blood cells, the problem of finding an objective threshold level is significantly reduced. The threshold can simply be chosen as the minimum level in which baseline noise is not counted as cellular events. The exit counter is used only qualitatively to see when cells have filled the capture region volume and to begin the reverse washing process.

Figure 18:
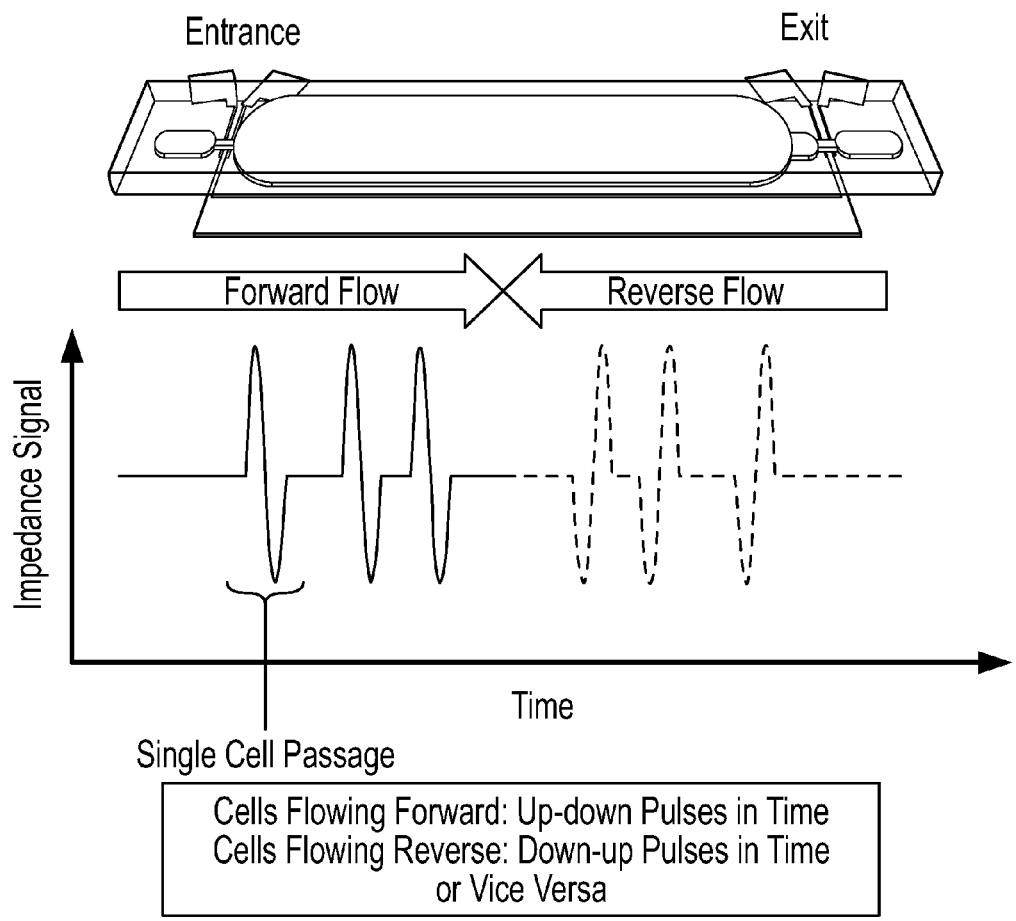
FIG. 18 is a schematic of a particle counting device and a graph of impedance signal as a function of time showing the signals caused by particles flowing in opposite directions.

The self-referencing sensor allows for easy discrimination between cells entering and exiting the entrance counter port. For example, depending on the external electrical configuration, a cell entering the entrance counter may create an up-down impedance pulse pair in time, while the same configuration will create a down-up signature for cells exiting under reverse flow past the entrance counter port (see, e.g., FIG. 18).

Figure 17:
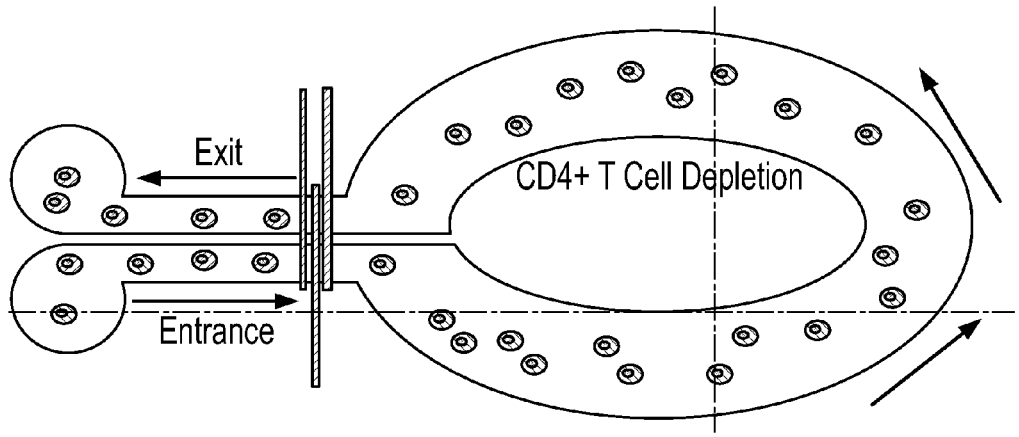
FIG. 17 is a schematic of a device using a single electrode set for counting cells flowing into and out of the capture chamber. The device includes a counting device in which a portion of the channel defines a flow path that extends in a loop from the first electrical differential counter through the capture chamber and back to the first electrical differential counter as shown in FIG. 17.

The improved accuracy of using a single electrode set for counting cells flowing into and out of the capture chamber described above with respect to the reverse flow implementation can also be provided by a counting device in which a portion of the channel defines a flow path that extends in a loop from the first electrical differential counter through the capture chamber and back to the first electrical differential counter as shown in FIG. 17. As discussed above with respect to FIG. 18, the pulse shape can be used to determine when cells are entering the chip and when cells are exiting the chip.

Obtaining Pure Leukocyte Samples from Whole Blood

Red blood cells can be lysed before flowing the cells through the differential counter chip. A lysis solution, e.g., of 0.12% (v/v) formic acid and 0.05% (w/v) saponin in DI, is used for erythrocyte lysis. A large excess of the lysis solution, e.g., 12 mL of lysis solution, is added to 1 mL of whole blood (drawn the same day and kept on a rotator at room temperature and incubated for 6 seconds with agitation). Lysis is immediately stopped by the addition of quenching solution (such as 5.3 mL of 0.6% (w/v) sodium carbonate and 3% (w/v) sodium chloride in DI) (see, e.g., D. Holmes, D. Pettigrew, C. Reccius, J. Gwyer, C. van Berkel, J. Holloway, D. Davies, and H. Morgan, Leukocyte analysis and differentiation using high speed microfluidic single cell impedance cytometry," Lab on a Chip, vol. 9, pp. 2881-2889, 2009). The solution is centrifuged for 5 min. at 200× gravity at room temperature, supernatant is aspirated, and pellet resuspended in 5 mL PBS+1% (w/v) bovine serum albumin (BSA). The quenching solution is centrifuged for 5 minute at 200× gravity at room temperature, supernatant is aspirated, and pellet resuspended in 5 mL PBS+1% (w/v) bovine serum albumin (BSA). The suspension is centrifuged again and resuspended in 1 mL PBS+1% BSA, giving the physiological concentration of white blood cells.

In a point of care implementation of the cell counting device 100, the red blood cell lysis could be performed on chip as described with reference to FIGS. 2A-2E.

Dynamic Threshold Analysis for Objective Enumeration of Cells

The impedance signal threshold level is the single most important variable in the electrical enumeration of cells in electrical differential counting; finding an objective method to choose the threshold is equally important. By definition, this threshold level determines whether impedance pulses are the entities of interest (cells, beads, etc.), or simply debris, electrical noise, or other entities that should be ignored during analysis. Generally, the threshold level can be based on integral multiples of the standard deviation of the baseline electrical signal when no cells are passing through the sensor region. In this way, most false positives from electrical noise are excluded when the threshold level is set at or above four to six times the standard deviation of the baseline signal level. However, choosing the threshold level based on electrical signal's standard deviation alone remains to be a subjective analysis method.

Even a small change in the threshold level can result in a large change in cell counts, especially at lower threshold levels. Listed below are some additional issues that can render this threshold scaling method impractical, because of large counting errors when performing differential counts; whether using the forward flow method with two counting electrodes (FIG. 5), the reverse-flow method with one counting electrode (FIG. 9), or other implementations (e.g., FIG. 17).

(1) A cell may not produce the same impedance pulse amplitude when passing through the second sensor in a forward flow, two-counter design or when passing back through the entrance counter in a reverse-flow, one-counter design. This introduces counting error because a cell may be counted entering the capture chamber, but not counted when leaving the capture chamber.

(2) The electrical noise level may vary enough during or between analyses to possibly trigger false positive counts if only a static threshold level was chosen.

(3) Debris or small entities (e.g., fragments of dead cells, platelets, etc.) may create impedance pulses with amplitudes that exceed the threshold, creating false positives.

(4) The optimal threshold levels may change from chip to chip because of the possible physical and/or electrical differences among fabricated chips. A static threshold level for all chips could result in inconsistent measurements that would seriously undermine the advantage of the microfabricated technology.

Figure 19A:
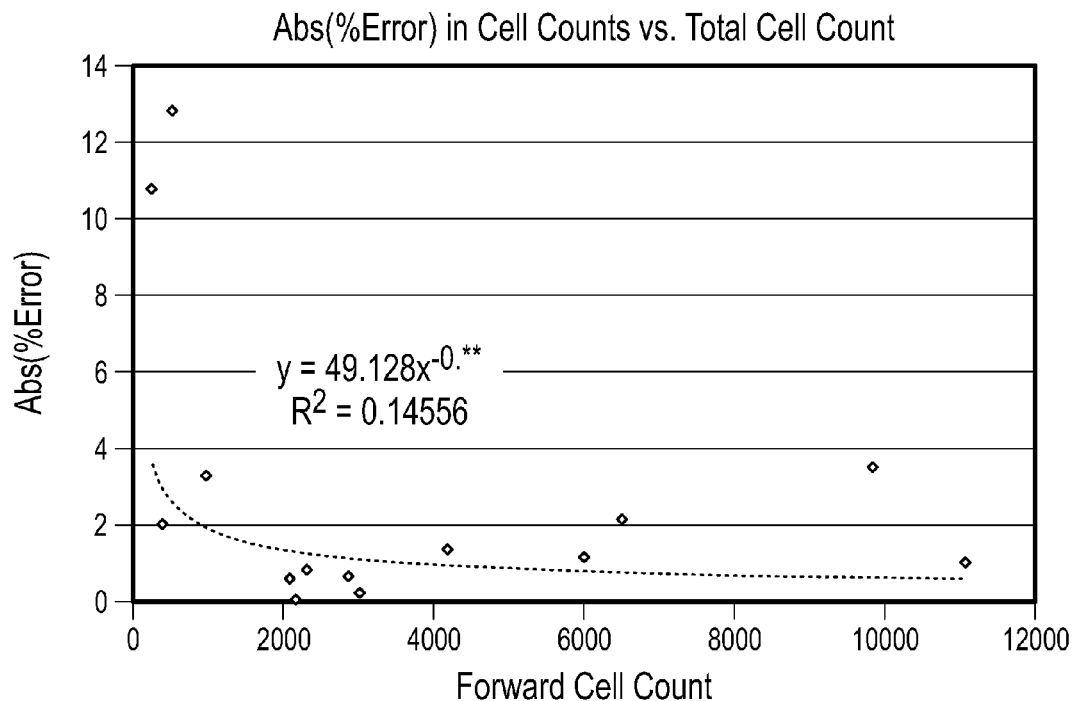
FIG. 19A is a graph comparing % error found using the reverse-flow differential counter protocol with the total number of cells counted.

The present solution for the task of objectively choosing a cell counting trigger threshold is to dynamically choose the proper threshold level by analyzing the impedance signal(s) with a range of discrete threshold levels. During or immediately after blood analysis, differential counts (i.e., entrance count-exit count, or forward count-reverse count) are plotted against their corresponding threshold trigger levels, and the optimal threshold level is chosen based on curve stability (i.e., "flatness"). This method has shown to have a low inherent counting error of ~9 cells·$\mu L^{-1}$ (FIG. 19A, Table 2).

Figure 22:
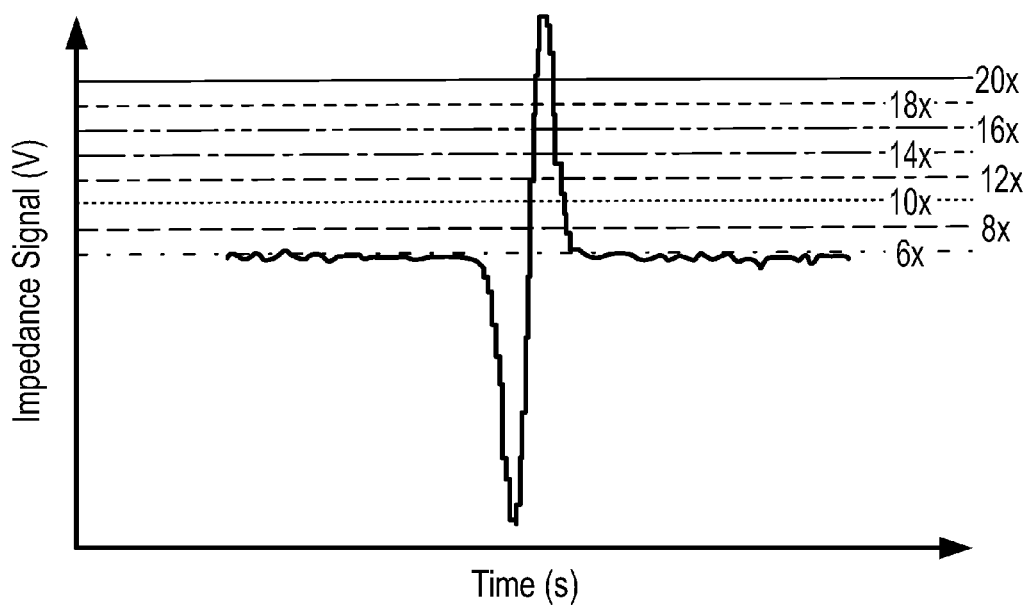
FIG. 22 is a graph that illustrates the generation of discrete impedance signal trigger threshold levels.
Figure 23:
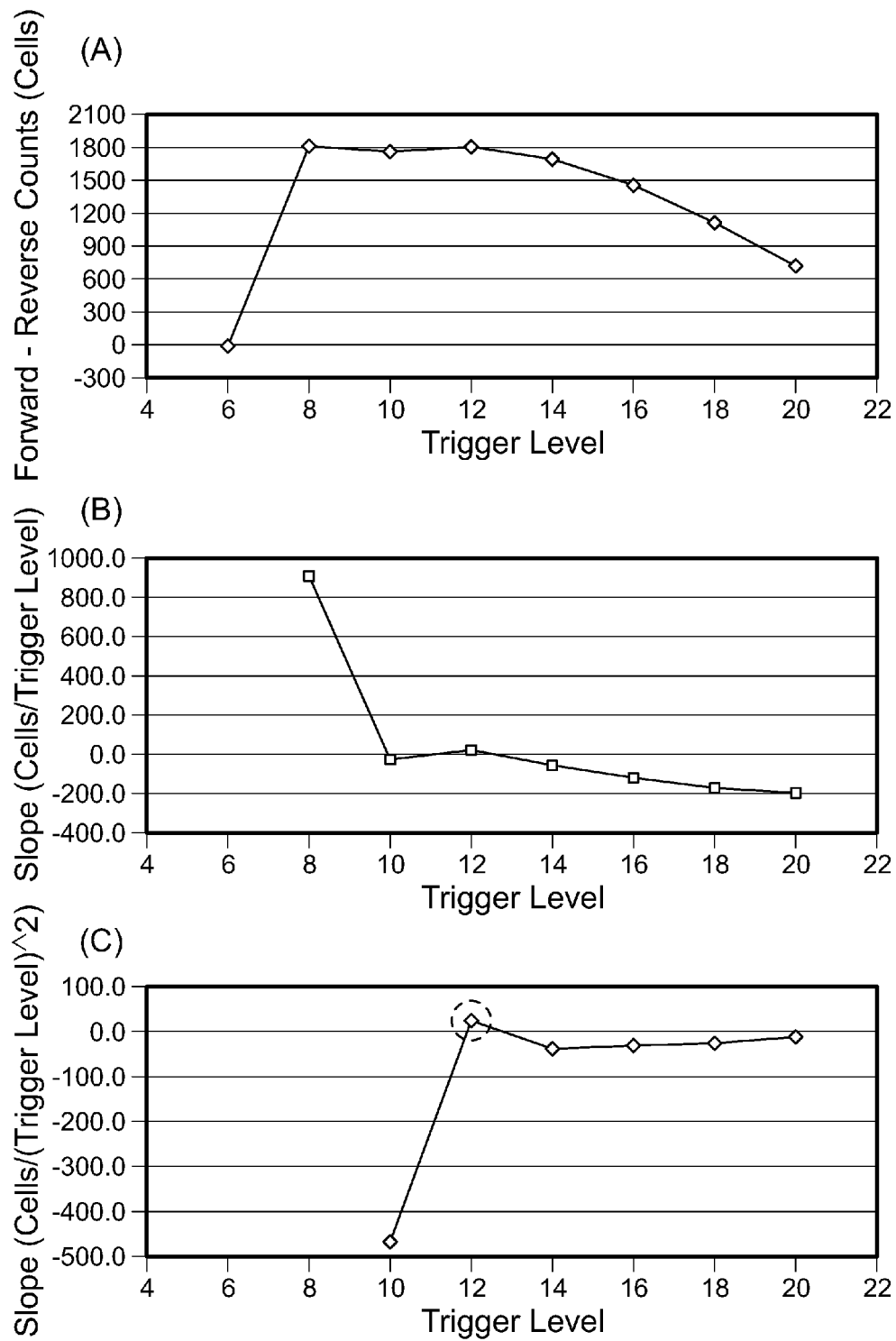
FIGS. 23A to 23C show the results of the dynamic threshold analysis procedure.
Figure 24:
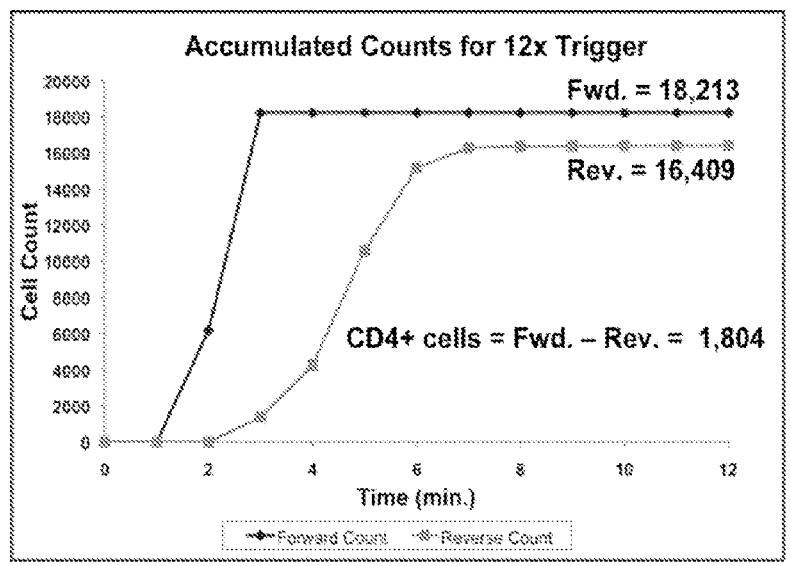
FIG. 24 is a graph that illustrates the cumulative forward and reverse counts for cells using the 12× trigger threshold level.

FIGS. 22, 23, and 24 illustrate this concept using data from an actual differential counting experiment.

First, discrete threshold levels are obtained. One method to create these levels is to obtain the standard deviation of the baseline impedance signal (before cell flow commences) to create a multiplicative standard (i.e., "1×" is the standard deviation). Trigger levels can either be calculated linearly (e.g., multiplication of the 1× standard), or through more complex, nonlinear methods. FIG. 22 shows a range of trigger threshold levels generated using the linear method, and how the 6× trigger (six times the standard deviation of the noise) encounters the baseline noise signal, which would result in false positive cell counts. The range (e.g., 6× to 20×) and multiplicative values (e.g., 6×, 6.5×, 7×, etc.) can be modified to ensure optimal analysis with proper dynamic range and resolution, respectively.

Second, the impedance signal(s) are analyzed with the generated range of trigger levels, and differential counts are plotted against their respective trigger levels. FIG. 23A shows the variation of differential CD4+ T cell counts for a range of threshold trigger levels (6× to 20×). In the ideal situation where each entity's pulse amplitude is identical for entering and exiting the capture chamber, the plot should be a horizontal line, showing that the differential counts are constant for all trigger levels. However, the smaller threshold levels encounter the signal's baseline noise level, creating many false positives that statistically conceal the true positives. The sudden increase in differential counts from 6× to 8× illustrates this non-ideality, as the 6× threshold level is too low in that it is falsely counting noise peaks as "cells." The differential count levels off at 8× and remains flat until 12×, where the counts gradually decreased. This plateau contains the optimal threshold trigger level and corresponding differential count because it best resembles the ideal horizontal line. Another deviation from the ideal plot is shown by the gradual decrease in the differential counts at larger trigger levels. This can possibly be explained that the average pulse height for the exiting entities is lower than the average pulse height for the entering entities (e.g., complication #1, listed above).

Third, the variation of counts between contiguous trigger levels is plotted to further investigate the most stable region of the count vs. trigger level curve. This is analogous to finding the slope of the plot in FIG. 23A, and is shown in FIG. 23B. Specifically, the slope values ($s_x$) are calculated from Equation 1:

$$s_x = \frac{(c_x - c_{x-1})}{(t_x - t_{x-1})} \quad (1)$$

where $c_x$ is the differential count and G is the trigger level at index x. In this case, x is limited to indices 2 to n, where n is defined as the total number of trigger levels used for analysis. Index 1 is excluded because, by definition, no slope can be calculated for index 1. Noteworthy: $s_x$ gives the slope immediately before the trigger value at index x.

Fourth, the variation in slope values between trigger levels is plotted to make the final stability assessment of the count vs. trigger level curve. This is analogous to finding the curvature of the plot in FIG. 23a (or equally the slope of the plot in FIG. 23b) and is shown in FIG. 23(c). Specifically, the variation in slope values ($v_x$) between two contiguous triggers is calculated from Equation 2:

$$v_x = \frac{(s_x - s_{x-1})}{(t_x - t_{x-1})} \quad (2)$$

In this case, x is limited to indices 3 to n. This is because no slope values exist to calculate the slope variation for indices 1 and 2. Noteworthy: $s_x$ gives the curvature immediately before the trigger value at index x.

Fifth, average curvature values are obtained for adjacent trigger levels to find the threshold level that is within the most stable regime of the counting analysis curve. The smallest average curvature corresponds to the optimal trigger level. Specifically, the average curvature ($a_x$) for two adjacent curvature values for a trigger level at index x is calculated using Equation 3:

$$a_x = \frac{|v_x| + |v_{x+1}|}{2} \quad (3)$$

In this case, x is limited to indices 3 to n−1, as curvature values are not available for indices 1, 2, and n.

The aforementioned methodology to identify the proper trigger threshold level can be succinctly described in the following steps:

1. Generate a range of discrete threshold values (FIG. 22).
2. Obtain differential counts for a range of threshold values, $c_x$ (FIG. 23A).
3. Find the count variation vs. trigger level, $s_x$ (FIG. 23B and Equation 1).
4. Obtain curvature vs. trigger level, $v_x$ (FIG. 23C and Equation 2).
5. Calculate averages of contiguous $v_x$ values (Equation 3).
6. Search for the minimum $v_x$ value and note its index, which belongs to the optimal threshold trigger level. The count for this index is chosen to be the actual differential count for diagnostic results.

Table 1 provides the data displayed in FIGS. 22A-C and is used to illustrate the dynamic threshold optimization process described above. The average curvature value at index 4 ($a_4$) corresponds to a 12× trigger level, resulting in a differential count of 1,804 CD4+ cells (selection highlighted in FIG. 23C). FIG. 24 shows the cumulative forward and reverse counts found using a 12× trigger level for the duration of the experiment.

TABLE 1

| Index (x) | Trigger Level (× 1× standard) | Differential Count ($c_x$) | Slope ($s_x$) | Curvature ($v_x$) | Avg. Curv. ($a_x$) |
|---|---|---|---|---|---|
| 1 | 6 | −7 | n/a | n/a | n/a |
| 2 | 8 | 1810 | 908.5 | n/a | n/a |
| 3 | 10 | 1759 | −25.5 | −467.0 | 245.5 |
| 4 | 12 | 1804 | 22.5 | 24.0 | 31.5 |
| 5 | 14 | 1693 | −55.5 | −39.0 | 35.4 |
| 6 | 16 | 1455 | −119.0 | −31.8 | 28.9 |
| 7 | 18 | 1113 | −171.0 | −26.0 | 19.4 |
| 8 (n) | 20 | 720 | −196.5 | −12.8 | n/a |

Figure 15:
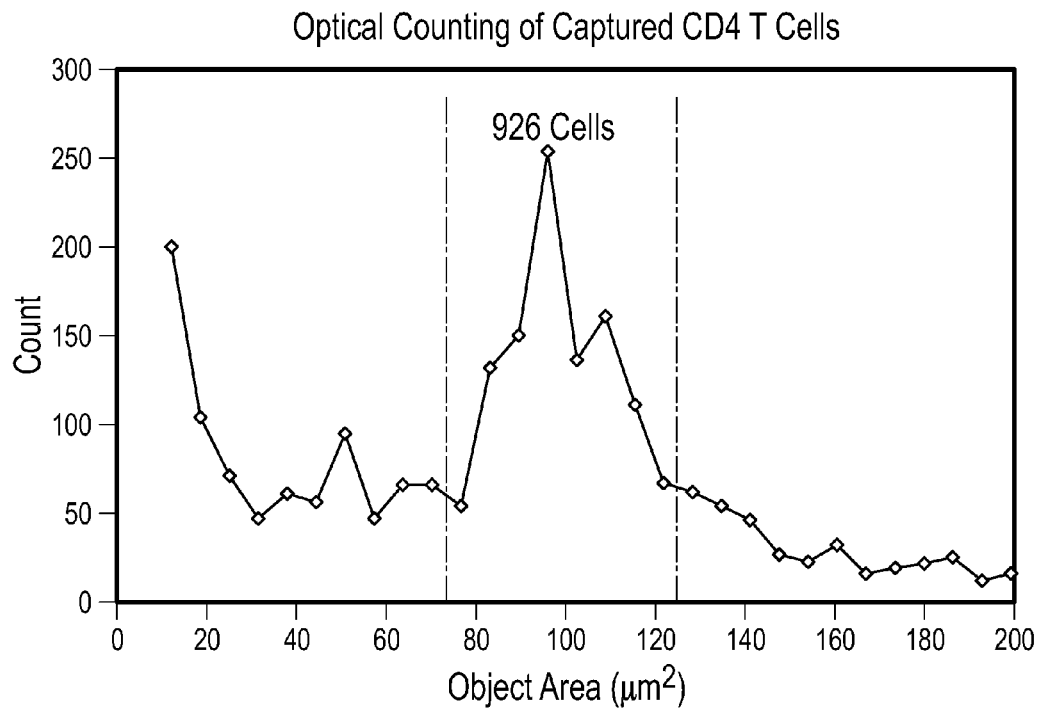
FIG. 15 is an area histogram of circular objects on a chip as observed using optical counting.
Figure 20A:
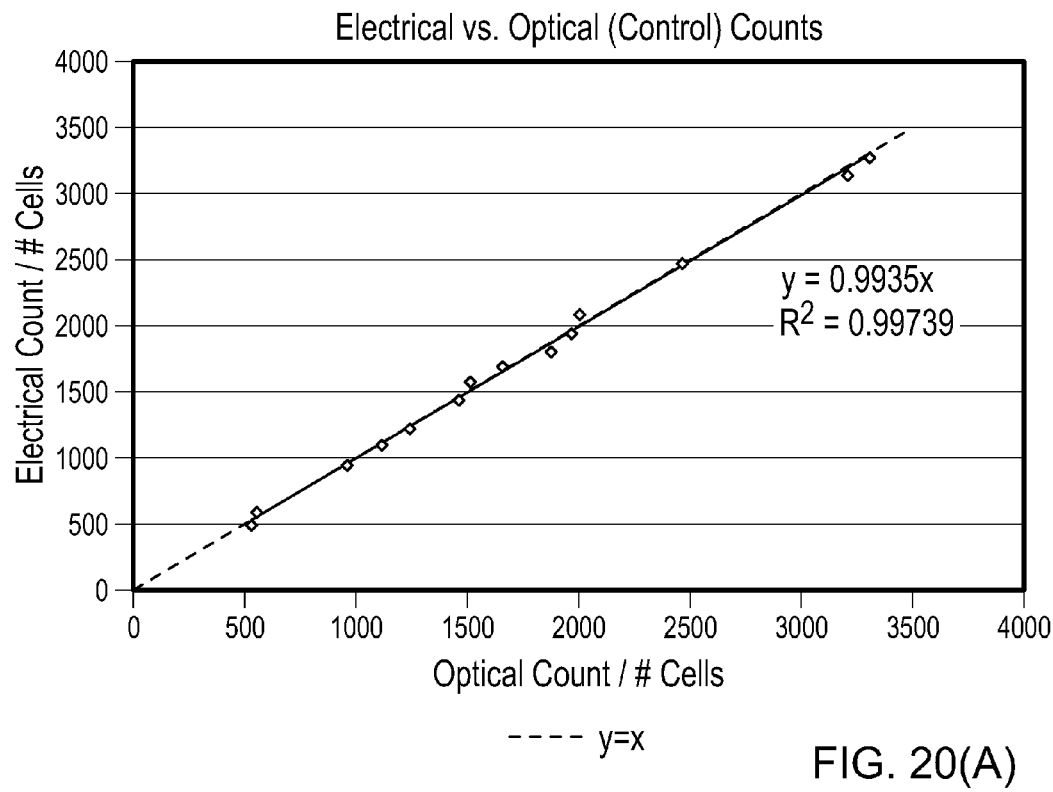
FIG. 20A is a graph comparing electrical and optical counts.
Figure 20B:
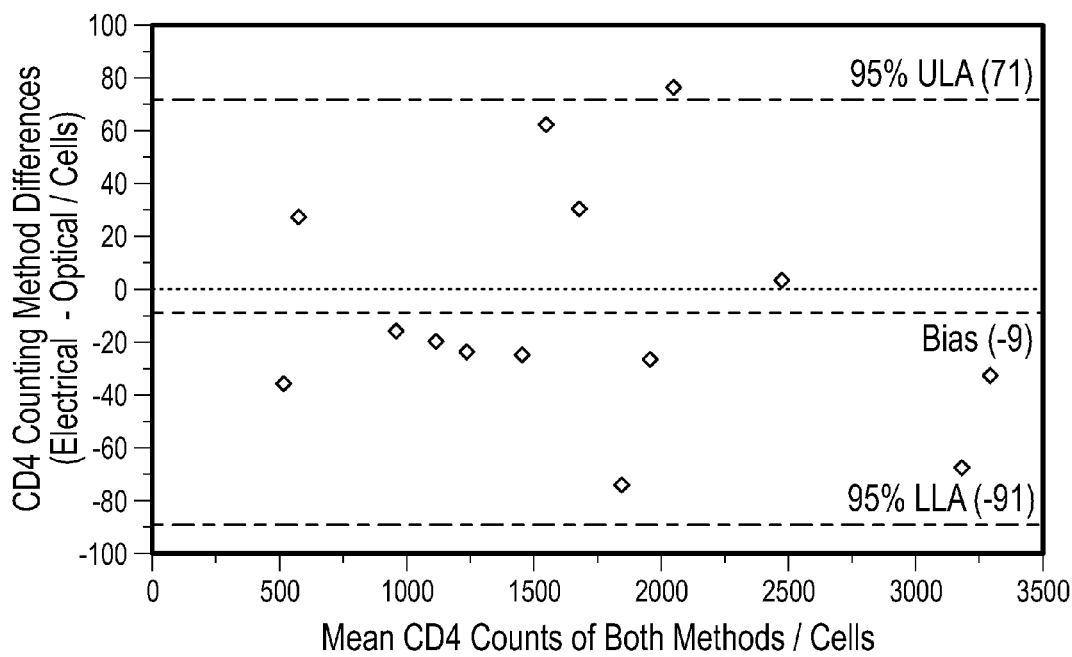
FIG. 20B is a graph depicting a Bland-Altman analysis of the data in FIG. 20A.

This dynamic threshold analysis method has been shown to provide counts which correlate closely (y=0.994x, $R^2$=0.997) with an optical enumeration method (FIG. 20A). This shows it to be a feasible method for the automatic enumeration of particles and cells using an electrical differential counting technique. FIG. 15 is an area histogram of circular objects on a chip as observed using the optical counting method. FIG. 20B shows Bland-Altman comparison analysis between the electrical differential and optical counting methods. A bias of only about 9 cells confirms the accuracy of the electrical differential counting method for the entire range of enumerated CD4+ T cells.

The aforementioned methods do not limit the scope of the dynamic threshold analysis method, but serve as an example to prove its feasibility and efficacy. The following are additional notes regarding other implementations of the dynamic threshold analysis method. First, integer multiples were used to generate discrete threshold values, but fractions of whole numbers can be used as well (e.g., 4.25×). Second, plotting the different data ($c_x$, $s_x$, $v_x$, $a_x$) is not necessary, but was used for illustrative purposes. The operating device's microcontroller or microprocessor would only need the raw differential counting data ($c_x$) to calculate the average curvature values ($a_x$). Third, analysis is not limited to Equations 1-3, as other implementations may be used to find the optimal thresholds more efficiently and/or effectively. Fourth, nonlinear methods can be used to generate threshold levels in addition to the linear method used in the above example. Fifth, threshold analysis is not limited to pulse amplitude (or height), but can be used on other variables, such as pulse width, pulse area, or other implementations. Sixth, threshold analysis is not limited to pulses with positive polarity, but can also be used for negative-going pulses. Seventh, the number of and spacing between threshold levels can be adjusted to provide a more accurate rendering of the threshold level vs. differential count plot to locate the optimal threshold level with higher precision.

Cell Counting Devices with Lysis and Quenching Regions

Figure 25:
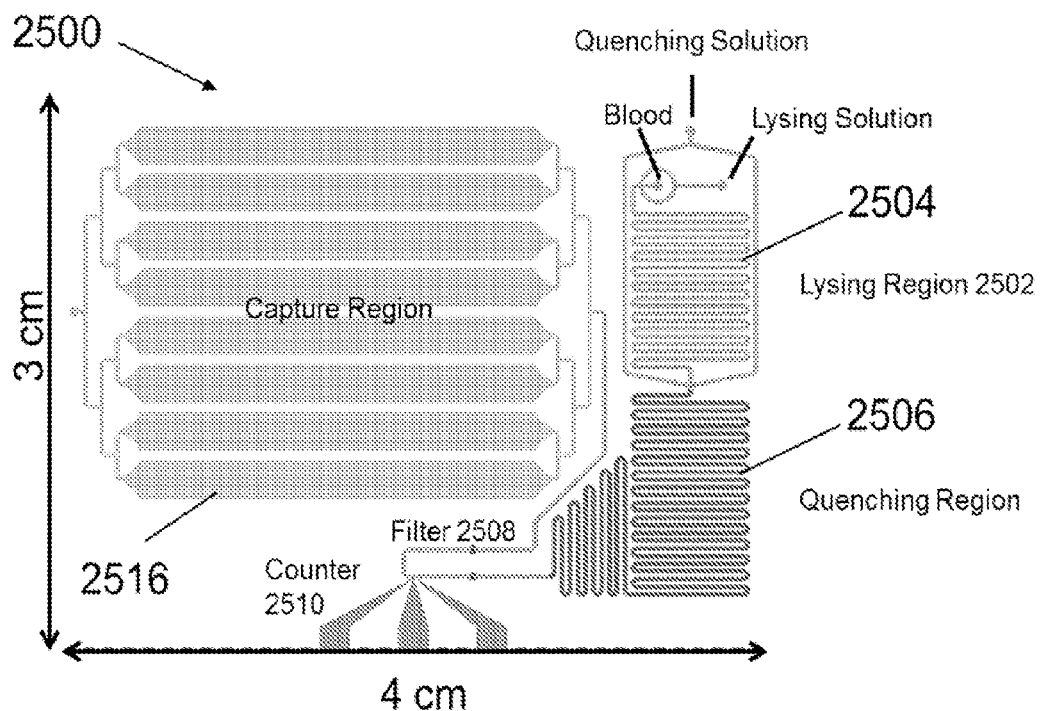
FIG. 25 is a schematic of a differential cell counter.

In some implementations, an on-chip lysis region, e.g., a red blood cell lysis region, can be included in the counting device, e.g., a CD4+ T cell counting device. The addition of the lysis region can eliminate requirements for additional laboratory equipment and personnel that are needed to lyse the red blood cells off-chip, enhancing the portability of the device. For example, FIG. 25 is a schematic that illustrates a CD4+ T cell counting device 2500 that incorporates a cell lysing region 2502 (e.g., for lysing red blood cells). During operation of the device 2500, whole blood flows into the chip and is surrounded by a lysis solution, which mixes in the serpentine mixing channels 2504 and rapidly ruptures the red blood cells within about 6 to about 10 seconds. Different conditions can be used to lyse other types of particles, e.g., cells. To ensure lysis during a desired time period, the volume of the lysis region channels and the flow rate of the lysis and sample, e.g., blood, solutions can be controlled. For example, the lysis region's channel width can range from about 50 μm to about 1 mm and height can be from about 10 μm to about 400 μm with lysis and blood solutions combined flow rates ranging from about 1 μL/minute to about 100 μL/minute.

Lysis is rapidly stopped to preserve the remaining cells, such as white blood cells, by the addition of a quenching solution and quench duration is extended via serpentine mixing channels 2506 to ensure quenching of the lysis process, which should have a duration of greater than about 10 seconds. The quenching channel dimensions and the combined flow rates of the lysing, blood, and quenching solutions can be controlled to ensure quenching duration is above this minimum. For example, the quenching channel dimensions can be formed to be similar to the lysis region channels and the combined flow rates of the lysis, blood, and quenching solutions can range from about 1 μL/minute to about 1000 μL/minute. The quenched solution then flows through a filter 2508 comprised of pores to prevent possible clogging of the counting pore having the same dimensions as the filter pores. The filter and counting pores can range in size from a height and width each of about 0.5 μm to about 50 μm.

The sensing electrodes of the counter 2510 can be made of a conduction layer of either platinum or gold or other high conductivity metal with an adhesion layer (optional) of chromium or titanium. The sensing electrodes can have widths and gaps ranging from less than about 1 μm to about 1 mm. The Coulter principle can be employed to electrically count cells individually by observing the temporal impedance changes (i.e., electrical pulses). White blood cells then pass through an identical filter before being distributed among eight identical capture chambers 2516, which can be from 10 μm to 100 μm high and 0.5 mm to 10 mm wide. The number of capture chambers 2516 can vary from 1 to over 32. Capture chamber height can be tailored to control the shear stresses at the fluid/chamber wall interface for optimal capture of CD4+ T cells or other cells/particles of interest.

The devices can be made with a glass substrate (with micro-patterned platinum or gold electrodes) bonded to PDMS (polydimethylsiloxane) fluidics via oxygen plasma treatment. Another method uses plastics for the substrate and fluidics (e.g., injection molding) with the sensing electrodes defined by laser ablation or similar processes.

Cell Counting Devices that Distinguish Between Different Types of Cells

In some implementations, the cell counting devices can differentiate between different types of white blood cells, red blood cells, and platelets based solely on using multiple interrogation frequencies. This technique enables counts of red blood cells, platelets, and white blood cell subtypes (monocytes, neutrophils, lymphocytes, etc.) in addition to the specific enumeration of CD4+ T cells using the antibody-coated capture chamber, as already described. For example, referring to FIG. 2, multiple signals of different frequencies can be applied simultaneously to one or more of the impedance sensors 110, providing a discrete impedance spectrum for any particular cell type.

Cells can be differentiated based on their different impedance spectra. For example, Holmes et al. used a 503 kHz frequency to obtain the volume of each cell, but also used a higher frequency (1.7 MHz) to simultaneously inspect a cell's membrane capacitance. They were able to differentiate among some of the different white blood cell subsets (monocytes, neutrophils, and T-lymphocytes) via observing the opacity of a cell (high frequency impedance divided by the low frequency impedance) with the assistance of a red blood cell lysis solution (see Holmes et al., "Leukocyte analysis and differentiation using high speed microfluidic single cell impedance cytometry," Lab on a Chip, 2009, 9, 2881-2889; see also Ledis et al., "Lysing reagent system for isolation, identification and/or analysis of leukocytes from whole blood samples," U.S. Pat. No. 5,155,044, October 1992). In addition, Cheung et al. used a 6 MHz frequency to differentiate between red blood cells and white blood cells (see, Chreung et al. "Microfluidic Impedance-Based Flow Cytometry," Cytometry: Part A, 2010, 77A, 648-666).

Accordingly, a low frequency (e.g., from about 1 kHz up to about 1 MHz) can be applied to the impedance sensors 110 to obtain a cell's volume and additional higher frequencies (e.g., from about 1 MHz to over 100 MHz) can be applied to the impedance sensors 110 to provide a discrete impedance spectrum for differentiating among several cell types. The more discrete frequencies used, the higher the resolution to differentiate between different cell types that can be indistinguishable at a smaller number of interrogation frequencies used. In particular, platelets can be discriminated among other cell types based simply on their size, as they are approximately 1 to 2 µm in size—much smaller than other cell types. As a result a low frequency measurement alone can differentiate platelets from other cell types. Red blood cells can be distinguished from white blood cells using a low frequency (500 kHz) and a high frequency (6 MHz), as red blood cells have a similar volume to the smaller white blood cells. In some implementations, different white blood cell types may require one or more frequencies in addition to the low frequency (500 kHz) for differentiation among the white blood cell subtypes.

EXAMPLES

The following examples are illustrative and not limiting.

Testing Maximum Pulse Density Limits

It is desired that the differential counter can enumerate the physiological concentration of white blood cells flowing at the desired range of 5-10 µL/min to provide a rapid helper T cell count. As the concentration of cells increases with a constant flow rate, the amount of average volume (and time) decreases between events (i.e., pulses caused by cell passage through the sensing region). Eventually, the concentration becomes high enough where two cells will be in the same sensing region, creating coincident events that reduce the accuracy of the counter. In addition, for a finite sampling frequency, even if the cells are not coincident in the sensing region, a high enough velocity will eventually cause overlap of the pulses from two subsequent cell passages.

Diluted whole blood was used to test the pulse density limits of the differential counter, because it contains an abundance of flexible particles, as opposed to polystyrene and latex beads, which have been prone to clog the counting channel. A constant flow rate of 5 µL/min was used to inject varying dilutions (1:1000 to 1:100) of whole blood into the chip. Pulses were only analyzed for the entrance counter. Pulse density was calculated by enumeration of pulses in known duration windows at random times throughout the raw data.

Figure 7:
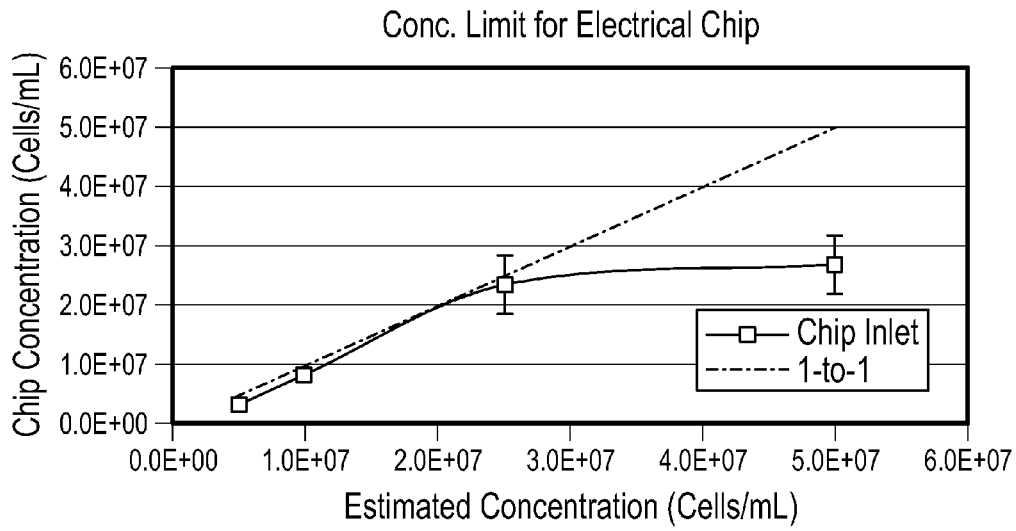
FIG. 7 is graph comparing estimated inlet concentrations with measured chip concentrations.

FIG. 7 illustrates the results as a comparison between the cell concentration found using the microfluidic chip (calculated by the number of pulses for a known volume flown) compared to the calculated concentration of each dilution (assuming a whole blood concentration of $5 \times 10^9$ cells/mL). At a 5 µL/minute flow rate, the microfluidic chip could handle the 1:200 dilution of whole blood ($\sim 2.5 \times 10^7$ cells/mL), but failed to count every pulse for the 1:100 dilution ($\sim 5 \times 10^7$ cells/mL). The maximum pulse density the chip could handle was 2,236 cells/s, equivalent to a concentration of $2.68 \times 10^7$ cells/mL at a flow rate of 5 µL/minute. This is well above the upper limit of leukocyte concentration in healthy adults, ensuring no coincident events, even at a flow rate of 10 µL/minute.

Testing Capture Chamber Sensitivity and Accuracy

The next experiments were done to verify that the entrance count is the same as the exit count for a passivated capture chamber. A 10 µL sample of healthy adult blood (with lysed erythrocytes) can have over 100,000 leukocytes, in which 10,000, or 10%, are helper T cells. A patient with AIDS can have helper T cell counts less than 200 cells/µL, which results in only 2,000 cells per 10 µL, or 2% of total leukocytes. Any errors in counting can negatively affect the sensitivity and accuracy of this method.

Before cells were flowed into the microfluidic chip, the capture chamber was passivated by flowing in PBS+1% BSA and incubating for 30 minutes at room temperature to prevent the non-specific adsorption of cells to the glass and PDMS surfaces. BSA is a well-known protein for surface passivation, and readily binds to the hydrophilic glass substrate at pH 7.4 (see e.g., Sweryda-Krawiec et al., "A new interpretation of serum albumin surface passivation," Langmuir, vol. 20, pp. 2054-2056, September 2004). In this particular experiment, three dilutions of white blood cells were flown into the chip at 5 µL/minute, followed by a 10 µL/min PBS+1% BSA wash to ensure all cells exit through the exit counter. Impedance data for each counter is recorded during the entire experiment.

Figure 8:
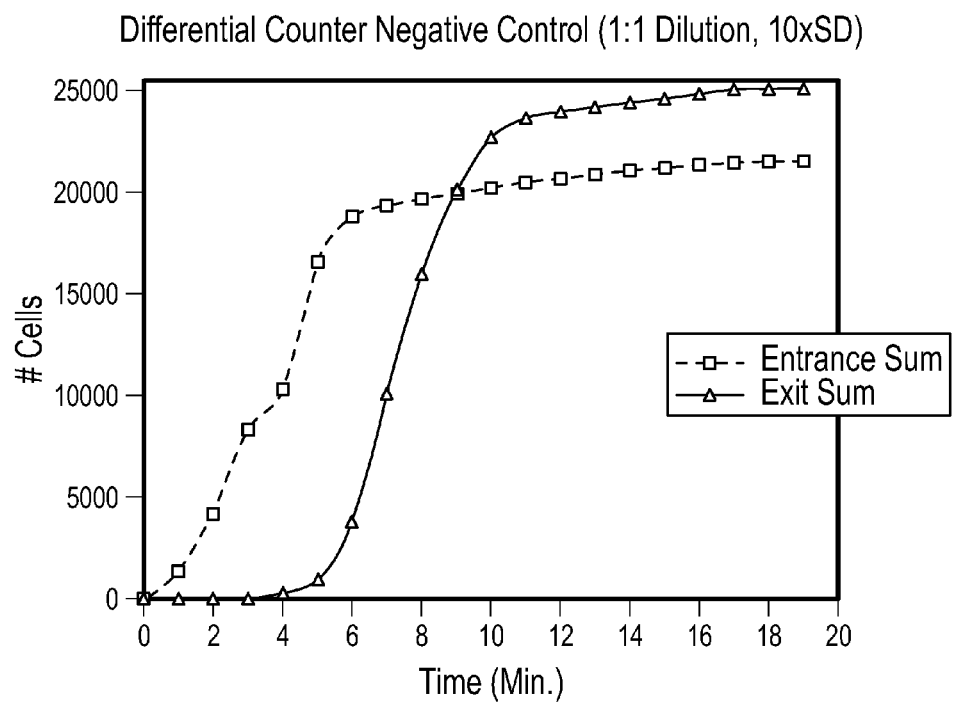
FIG. 8 is a graph presenting entrance and exit counts for a passivated capture chamber experiment.
Figure 9:
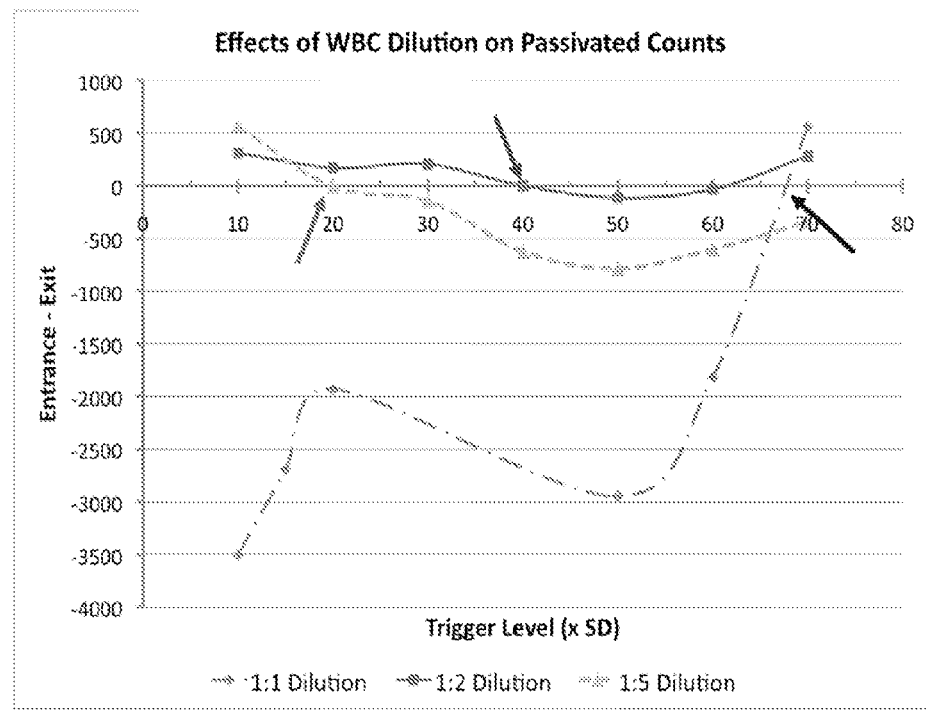
FIG. 9 is a graph illustrating the relationship between white blood cell concentration and the discrepancy between the entrance and exit counts.

FIG. 8 illustrates a typical result for the negative control experiment. Ideally, the entrance and exit sums should be equivalent at the end of the experiment, but have a difference of over −3,500. It was interesting to note that the exit count was higher than the entrance count, which is true for the 1:1 dilution of white blood cells, but not as dominant in the lower dilutions. FIG. 9 shows the relationship between the white blood cell concentration and the difference between the exit and entrance counts for various trigger levels. A trigger level is the voltage threshold that determines whether an impedance pulse is a cell, and is set manually in Clampfit.

It is a common convention to base the trigger level on the standard deviation of the baseline signal's noise (with no cells present).

In this experiment, a trigger level of ten times the standard deviation (SD) of the noise was the minimum threshold that could be used to ensure baseline noise pulses were not counted as cellular events. The threshold level for the entrance and exit counters was identical. A noticeable trend is the less diluted samples intersect the X-axis (Entrance-Exit=0) at higher threshold values (67×SD for 1:1; 40×SD for 1:2; 20×SD for 1:5) in the direction of increasing trigger level value (left to right). This, combined with the fact that the exit count is higher than the entrance count, can explain the large discrepancy in the entrance and exit counts. Cell aggregates form more frequently as the concentration of the purified leukocytes increases, because there is more interaction between cell surfaces. These aggregates pass through the entrance counter port and its relatively high shear stresses (1,320 dyne/cm) separate the aggregates back into individual cells, which are then counted by the exit counter. An aggregate is counted as a single entity by the entrance counter, but can become three or more entities by the time it reaches the exit counter. The entrance and exit counts only become equal when the threshold level is large enough to not count smaller entities such as single cells, and only counts larger objects that remain physically intact after passing through the entrance counter.

Figure 10:
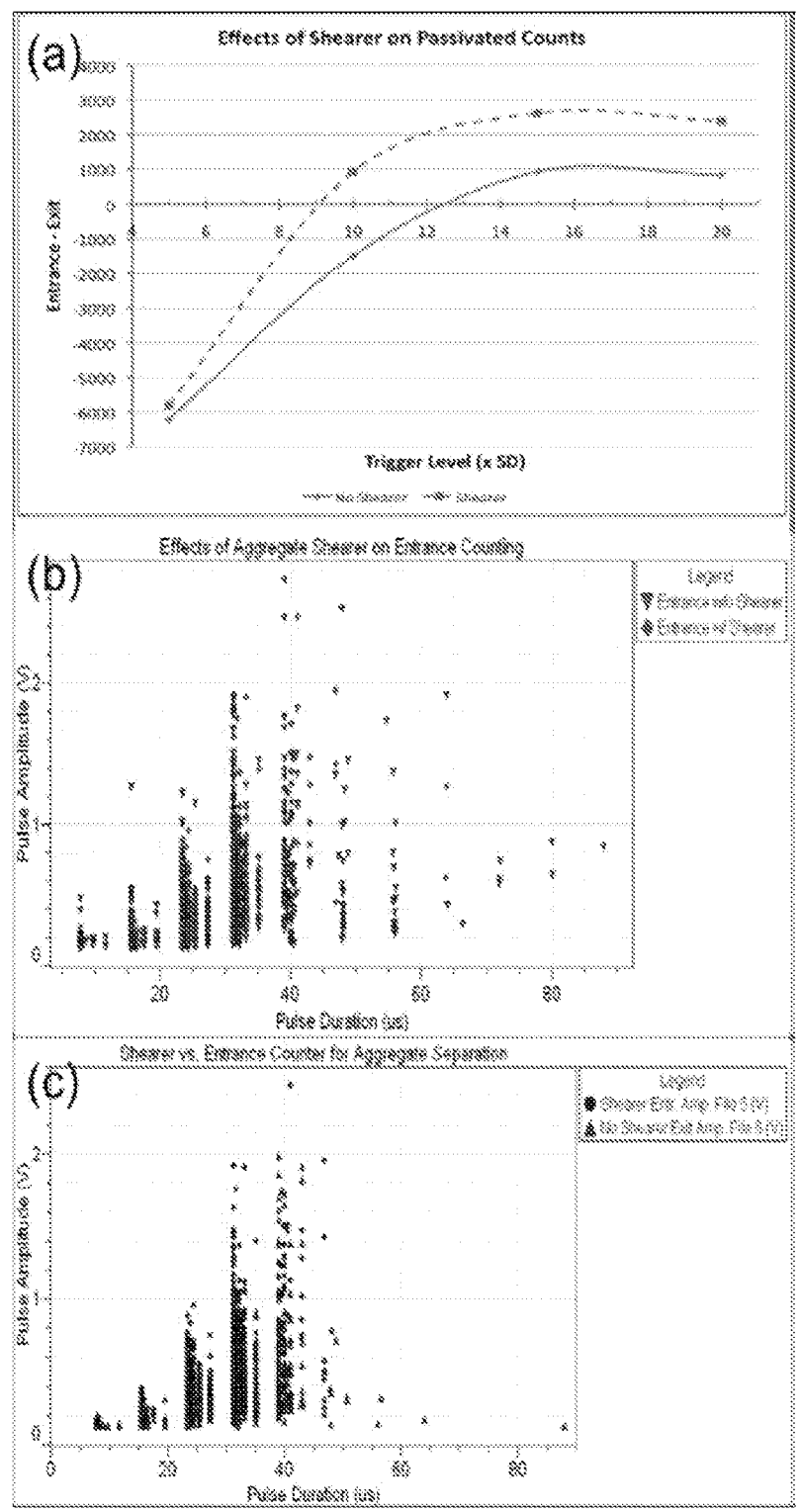
FIGS. 10A to 10C are a series of graphs illustrating the effect of including a shearing module in a cell counter.

The aggregation of leukocytes prevents a true evaluation of the differential counter and can be remedied by larger dilutions. However, diluting has several drawbacks, most importantly, analyzing only a fraction of the cells needed to provide a more robust helper T cell test and requiring a much larger chip volume. Therefore, it is desirable to have physiological concentration of white blood cells enter the chip, and can possibly still be allowed using a microfabricated 10 μm×13 μm PDMS/glass pore, or "shearer," to separate cell aggregates before the chip entrance. FIG. 10A shows the results after repeating the passivated experiment for 1:1 diluted leukocytes. The shearer proves to decrease the number of aggregates before entering the differential counter chip (X-intercept at 9×SD vs. 12.5×SD for cell samples injected directly into the chip without the shearer).

FIG. 10B shows the difference in cell size (pulse amplitude) and cell passage duration when using the shearer. The population undergoing shear before making it to the entrance counter is a tighter distribution at lower pulse duration with similar pulse height amplitude as the unsheared population because the larger aggregates block the impedance sensing region longer. The amplitude does not change much because even the single cells are large enough to block most of the electrical current passing between the sensing electrodes.

FIG. 10C illustrates the size and passage duration similarities of cells that have been sheared prior to and counted at the entrance sensor and cells that did not undergo pre-chip shearing, but pass through the entrance counter pore and are counted at the exit counter. This shows that the entrance counter indeed is shearing aggregates into smaller entities, performing the same job as the pre-chip shearer. It is therefore necessary to have the shearing unit placed before the chip to ensure most aggregates are separated into single cells.

Testing a Reverse-Flow Differential Counter

Figure 12:
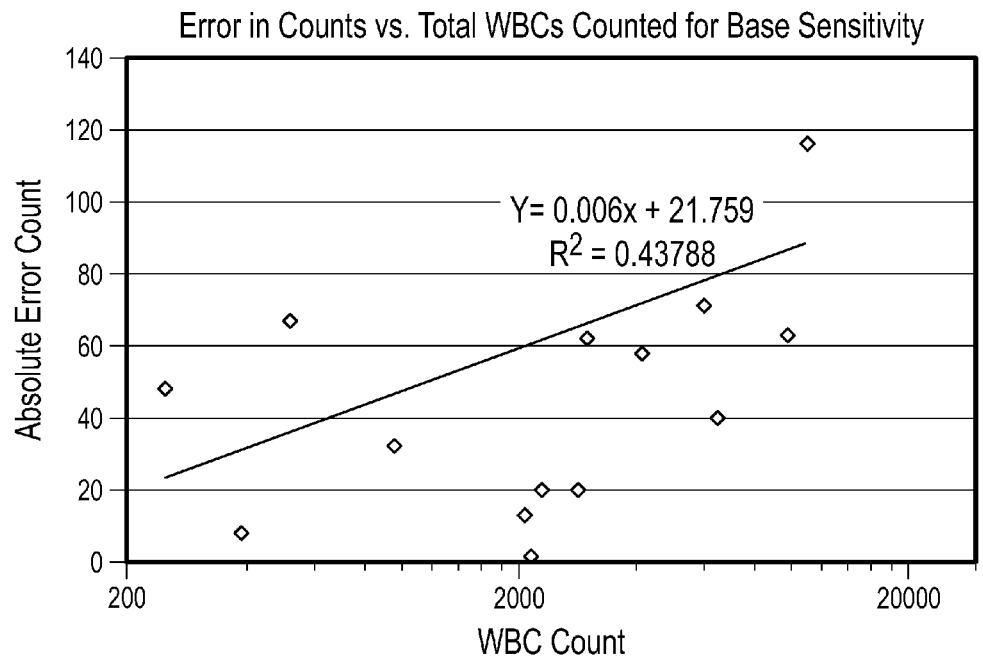
FIG. 12 is a graph comparing the error in counts found using the reverse-flow differential counter protocol with the total number of cells counted.
Figure 13:
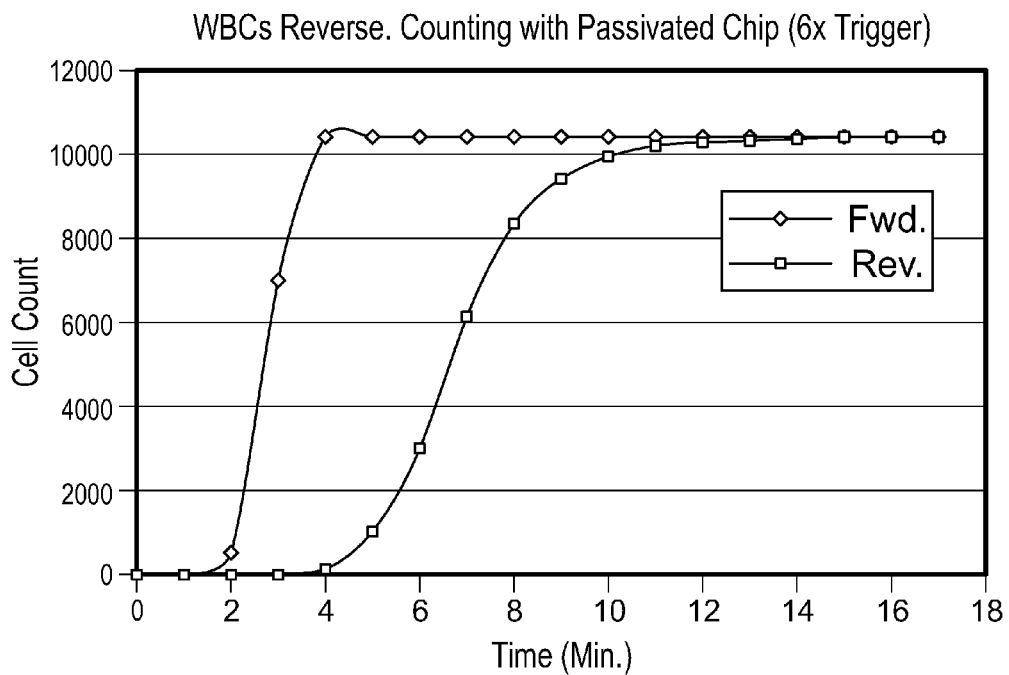
FIG. 13 is a graph presenting entrance and exit counts for a passivated capture chamber experiment using the reverse-flow differential counter protocol.

The passivated capture chamber experiments noted above were repeated using the reverse-flow protocol, and the results of fourteen different experiments are shown in FIG. 12 and FIG. 19A. The forward count is equivalent to the number of leukocytes that entered the capture chamber during forward flow; the absolute error count is the difference from the ideal differential count of zero; the percent error is the absolute error count normalized by the forward count. FIG. 12 shows how the absolute error count remained roughly constant for the entire forward counting range. This resulted in a decreased percent error for larger forward counts (FIG. 19A), which is desirable. FIG. 13 is a graph presenting entrance and exit counts for a passivated capture chamber experiment using the reverse-flow differential counter protocol.

Figure 19B:
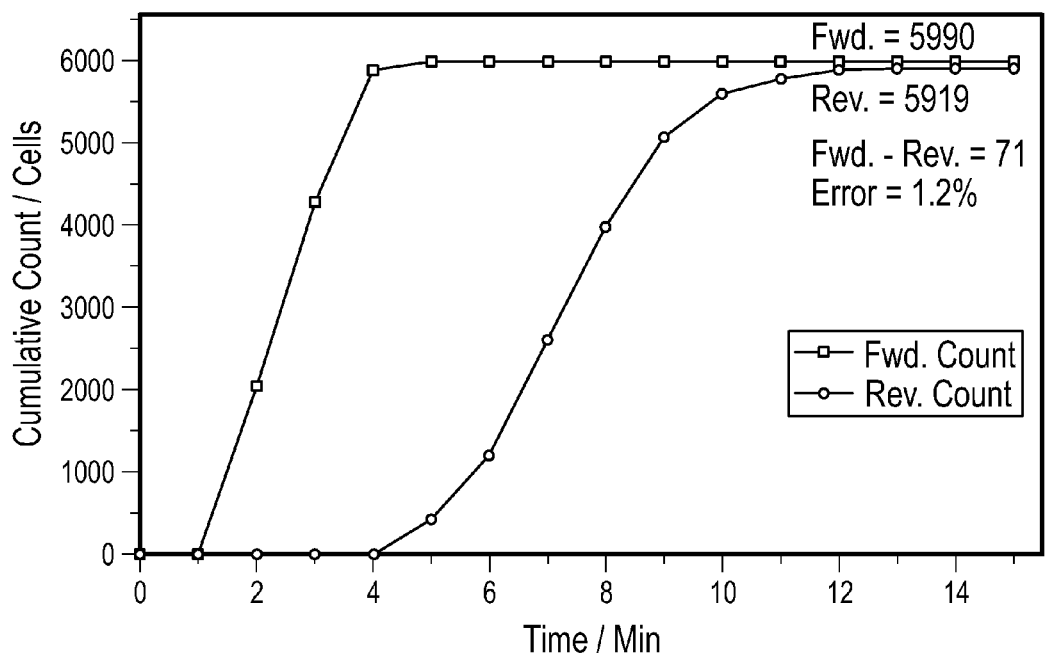
FIG. 19B is a graph that illustrates the cumulative forward and reverse counts for cells using the reverse-flow differential counter protocol.

FIG. 19B illustrates the accumulated forward and reverse counts during the experiment highlighted in FIG. 19A. This demonstrates how the reverse count eventually leveled off and became close to the forward count. As Table 2 below shows, forward counts greater than 2,000 resulted in a much smaller error. This ensures that larger leukocyte numbers—found in clinical situations—will result in the lowest error. The decreasing % error for increasing total forward cell counts can be explained by the fact that the counting errors do not scale with the total number of cells flown, and remain relatively constant.

TABLE 2

| Data Range | Error (%) (FIG. 12 inset) | | Abs. Counting Error (cells) (FIG. 12) | | Est. Sensitivity (cells · μL$^{-1}$) | |
|---|---|---|---|---|---|---|
| | $\bar{x}$ | SD | $\bar{x}$ | SD | $\bar{x}$ | SD |
| All WBC | 2.91 | 3.93 | 44.2 | 31.3 | 8.84 | 6.26 |
| WBC < 2000 | 7.25 | 5.37 | 38.8 | 25 | 7.76 | 5 |
| WBC > 2000 | 1.18 | 1.02 | 46.4 | 34.5 | 9.28 | 6.9 |

Table 2 summarizes the data from FIG. 12 and FIG. 19A for different ranges of total white blood cells counted. The estimated sensitivity can be obtained by assuming approximately 5 μL of sample was flown into the chip (approximate because current metering methods are in need of improvement). As a result, base sensitivity is ~9 cells/4 for the more realistic range of greater than 2,000 white blood cells counted, which is similar to the best sensitivity in electrical CD4+ T cell counts in the literature (Cheng et al., "Cell detection counting through cell lysate impedance spectroscopy in microfluidic devices," Lab on a Chip, vol. 7, pp. 746-755, 2007). The main source of counting errors was caused by non-specific adsorption of cells onto the chamber surface, despite passivation with BSA. A more successful passivation using more incubation time and/or PBS with a pH closer to BSA's isoelectric point of 5 would substantially decrease this error and illustrate that the differential counting method would provide the most sensitive enumeration technique (Freeman et al., "Real time, high resolution studies of protein adsorption and structure at the solid-liquid interface using dual polarization interferometry," Journal of Physics: Condensed Matter, vol. 16, pp. S2493-S2496, 2004). Another possible source of error may be dead/dying cells rupturing under the high shear rates found in the counter channel after forward counting.

Enumeration of CD4+ T Cells Using the Reverse-Flow Technique

The reverse-flow technique was used to electrically enumerate the number of CD4+ T cells captured on a microfluidic chip. The capture region was first coated with an anti-CD4 antibody (Ab)(1:10 in PBS) by adsorption for 30 minutes, followed by several iterations of flowing in more Ab and waiting 10 minutes between each iteration. Unbound Ab was removed by rinsing the chamber with PBS+1%

BSA, which also passivates any surface which does not have Ab adsorbed to it. White blood cells were flown into the chip at 5 μL/minute until cells were electrically detected at the exit counter. PBS+1% BSA was then infused through the exit counter port initially at 5 μL/minute to increase the interaction time between the helper T cells and the CD4 Ab. The washing flow rate was increased to 10 μL/minute after most cells had exited the chip to wash away any non-specifically bound cells.

Figure 14:
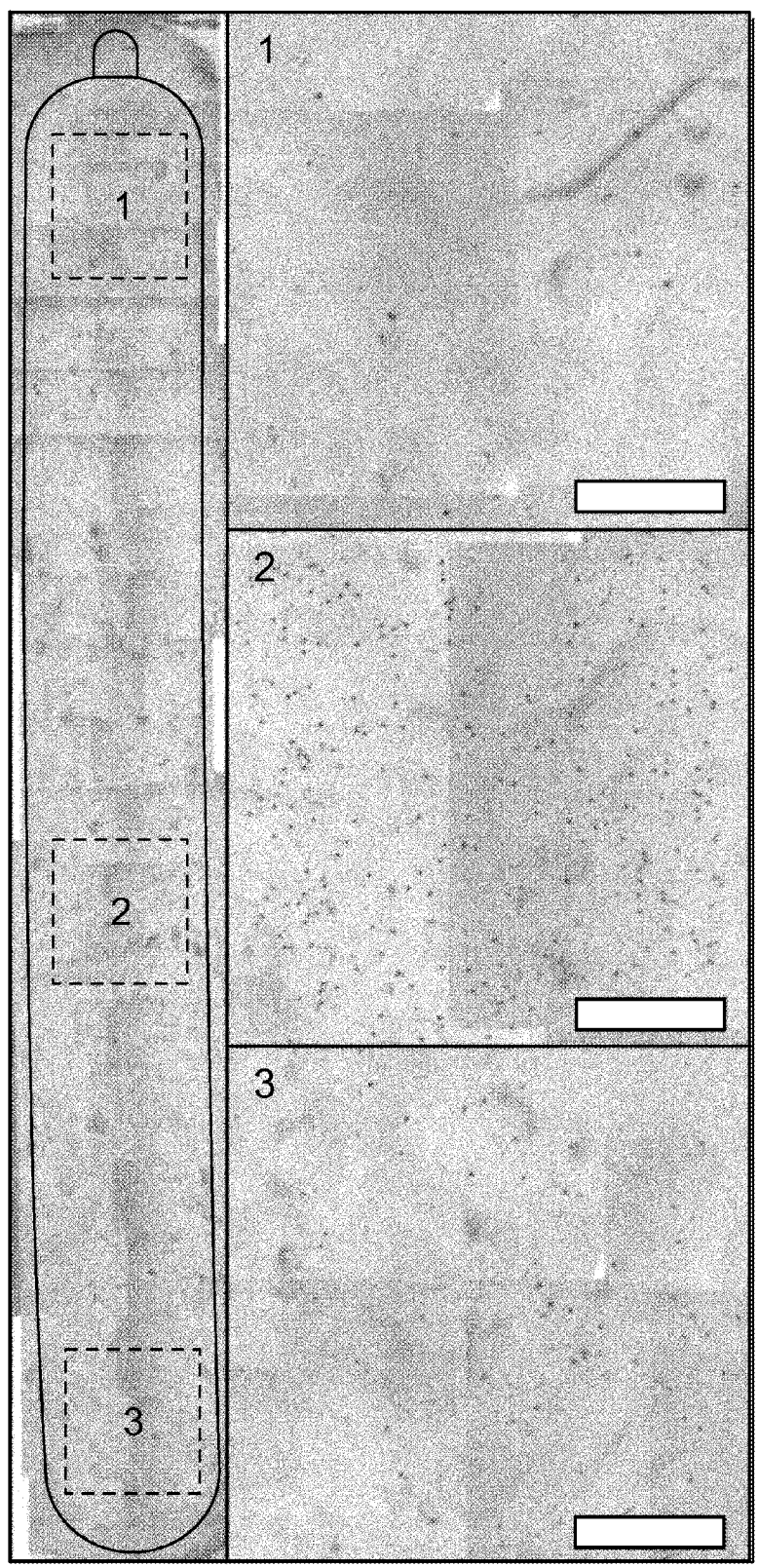
FIG. 14 is a series of merged images of an entire differential counter chip with magnification of regions near the entrance (1), mid-section (2), and exit (3).

After electrical counting, an optical control was obtained by imaging the captured cells for subsequent enumeration using image processing software. Phase contrast images of the entire capture region were taken using an Olympus IX81 inverted microscope at 40× total magnification. The 42 images were aligned and merged using Adobe Photoshop image processing software, and cells were counted using ImageJ software. FIG. 14 shows the merged images and resultant image of the entire capture and counter regions. It was found that the highest density of captured cells was found before the midpoint of the capture chamber's length (inset 2). A smaller density of cells were found near the inlet (inset 1), which is expected since the cells have not had enough time to interact with the Ab on the chamber surface. The lowest density is found near the exit of the chamber, where very few cells are attached (inset 3). Most likely the washing process began before the higher concentration of cells made it to the exit, but could also be because the majority of the helper T cells had ample time to bind to the immobilized CD4 Ab.

It was also noted that the cell path does not span the entire width of the capture channel. This results because the relatively narrow counter channel acts as a highly-focused nozzle which causes most of the cells to travel within ±850 μm of the centerline of the channel's length. This can be resolved by placing the entrance and exit counters diagonally opposite of each other (in opposite corners of the capture chamber), which would force the cells to travel the diagonal length of the capture chamber. Another solution may simply be found by curving or fanning the counter outlets so that the cells will not be as focused once entering the capture chamber.

FIG. 15 shows the automated counting of circular objects of various internal areas. The dotted lines denote the range of areas assumed for the helper T cells and gives a helper T cell count of 926. This range encompasses cell diameters from 10 to 12.5 μm, which is somewhat larger than the diameter of lymphocytes reported in the literature, but these cells are not in optimal physiological conditions and may have initiated apoptosis. Also, the phase contrast imaging creates a halo around the cell diameter, which could cause an apparently larger cell, especially when taken at a low magnification, where the size of the pixels are relatively larger and may not create an accurate representation of the cell's perimeter.

Figure 16:
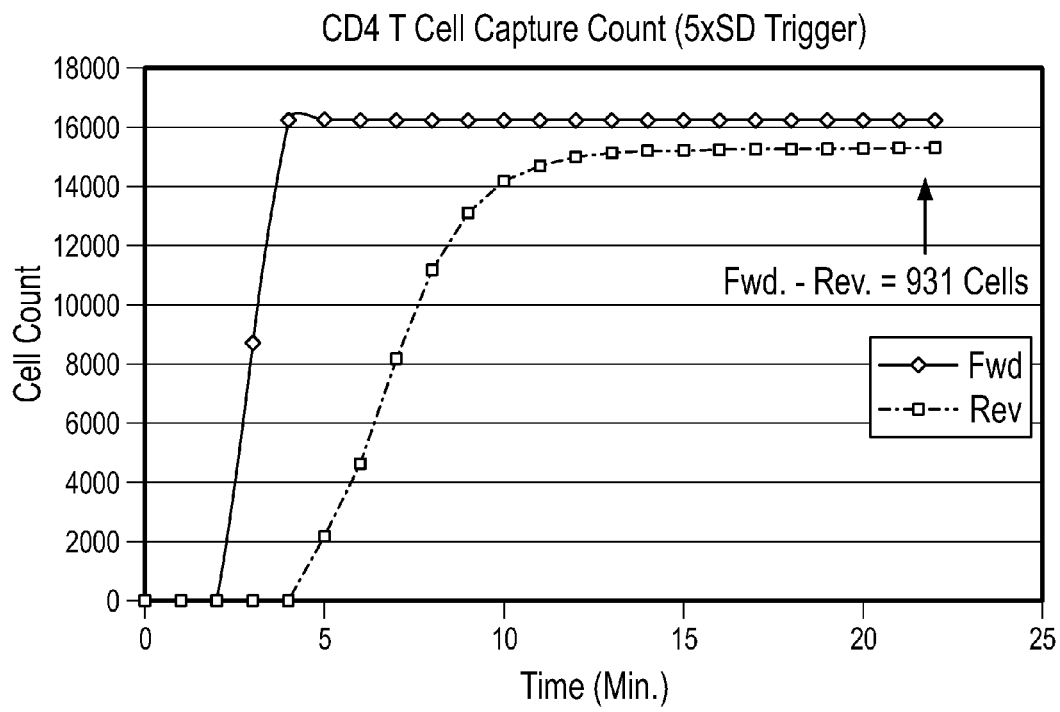
FIG. 16 is a graph presenting forward and reverse flow counting of CD4+ T cells.

FIG. 16 shows the results of the reverse-flow differential counting of captured helper T cells. The obtained count of 931 cells closely matches the count found by image processing, and shows that the differential counter method is viable method of enumerating helper T cells in a microfluidic chip.

Figure 21:
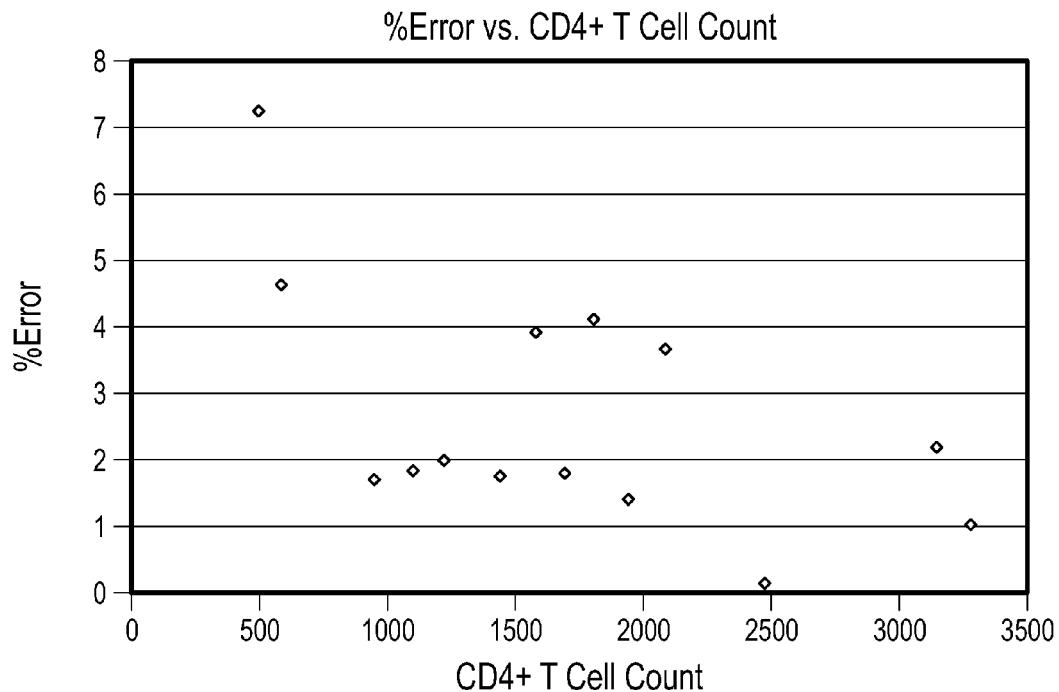
FIG. 21 is a graph comparing % error with CD4+ T cell counts.

FIG. 20 shows results from 14 CD4+ T cell counting experiments using white blood cells purified from human whole blood samples and the close correlation (y=0.994x, $R^2$=0.997) between the electrical differential method and the optical control. FIG. 21 illustrates how the percent error (absolute difference in optical and electrical counts, normalized by the CD4+ T cell count) relates to the total number of CD4+ T cells counted. For less than 1,000 cells captured on the chip, the average error is 4.5% (n=3). Assuming a 5 μL sample volume, this would be for CD4+ T cell concentrations less than 200 cells/μL, the concentration limit which defines AIDS. This shows to be highly accurate, as a patient with an actual CD4+ T cell concentration of 100 cells·μL$^{-1}$ would have a counting error of only +/−4.5 cells/μL. For counts above 1,000 cells captured in the entire chip, the average error is 2.1% (n=11). The 25+/−10% (n=14) ratio of captured cells to total cells counted agrees with the literature concerning the 25-33% of leukocytes being CD4+ T cells (Daniels et al., "Functional histology: A text and colour Atlas," Churchill Livingstone, 1979).

Cell Counting Using Device with Lysing and Quenching Regions

Experiments were set up to evaluate the reverse electrical differential counting method with the additional red blood cell lysing and quenching regions to ensure its feasibility in diagnostics testing using the device 2500 described above. The chip's capture regions and exit holding coil were passivated from cellular interactions using a 1% BSA (bovine serum albumin) solution in PBS (pH 4.5) for three hours. The holding coil was used to ensure cells exiting the chip during forward flow direction would not be lost to waste before flow reversal. Various sample sizes of whole blood (0.5 to 10 μL) were injected into the chip at a flow rate of 1.5 μL/min. The lysing solution (0.12% (v/v) formic acid and 0.05% (w/v) saponin) and quenching solution (2×PBS and 0.6% sodium carbonate) were infused at 17.5 μL/min and 8.5 μL/min, respectively, using an HPLC pump. Flow was reversed once the desired blood volume was injected and the experiment duration ended when cells were completely washed from the chip and holding coil.

Figure 26:
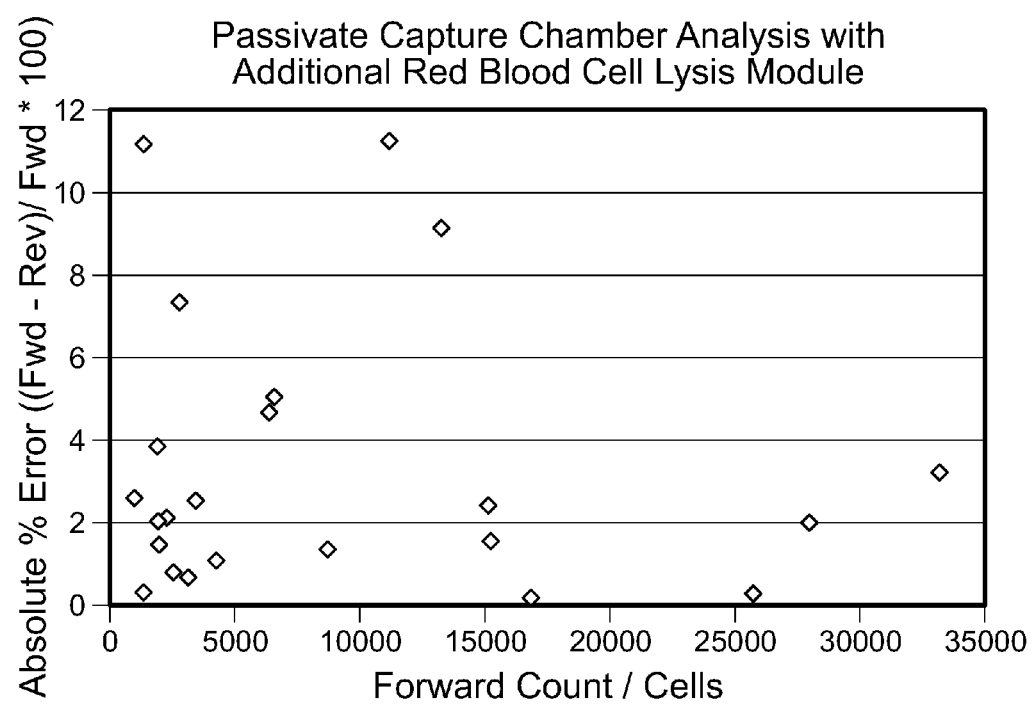
FIG. 26 is a plot of percent error of differential cell counts for whole blood samples.

FIG. 26 illustrates the percent error of twenty-three differential cell counts for whole blood samples. The percent error is calculated as the absolute difference between the forward and reverse counts, normalized by the forward count, and multiplied by 100. Ideally, the forward and reverse counts would be identical, resulting in a percent error of 0%. The average percent error for all twenty-three experiments was about 3.3%, which is similar to the percent error of about 2.9% in the previous implementation that did not have a red blood cell lysis and quenching module (Table 2). This shows that the differential counting chip with the addition of the red blood cell lysis and quenching modules results in a feasible device that can analyze unprocessed whole blood samples with low inherent error—making it practical for the use as a portable diagnostic device.

OTHER IMPLEMENTATIONS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A device comprising:
a microfluidic chip defining a channel including an inlet and an outlet;
a capture chamber arranged along the channel between the inlet and the outlet, wherein the capture chamber comprises a surface functionalized or coated with binding agents or binding moieties selected to specifically bind to a first type of particle of interest from fluid flowing through the channel;

a first electrical differential counter arranged to count all types of particles in a fluid flowing into the capture chamber and to count all types of particles remaining in the fluid flowing out of the capture chamber, wherein a portion of the channel defines a flow path that extends in a loop from the first electrical differential counter through the capture chamber and back to the first electrical differential counter; and a computer in electronic communication with the first electrical differential counter, wherein the computer calculates a number of the first type of particle of interest based on a difference between signals from the first electrical differential counter.

2. The device of claim 1, further comprising a pump system in fluid communication with the channel, wherein the pump system is operable in a first mode to cause fluid to flow in a first direction in the channel past the first electrical differential counter and operable in a second mode to cause fluid to flow in a second direction in the channel opposite the first direction and back to the first electrical differential counter.

* * * * *